(12) United States Patent
An et al.

(10) Patent No.: US 9,375,152 B2
(45) Date of Patent: Jun. 28, 2016

(54) HEART SOUND DETECTION SYSTEMS AND METHODS USING UPDATED HEART SOUND EXPECTATION WINDOW FUNCTIONS

(71) Applicant: CARDIAC PACEMAKERS, INC., St. Paul, MN (US)

(72) Inventors: Qi An, Blaine, MN (US); Pramodsingh Hirasingh Thakur, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 366 days.

(21) Appl. No.: 13/767,362

(22) Filed: Feb. 14, 2013

(65) Prior Publication Data

US 2013/0237773 A1 Sep. 12, 2013

Related U.S. Application Data

(60) Provisional application No. 61/607,791, filed on Mar. 7, 2012.

(51) Int. Cl.

| | |
|---|---|
| *A61B 5/0205* | (2006.01) |
| *A61B 7/00* | (2006.01) |
| *A61B 5/00* | (2006.01) |
| *A61B 5/024* | (2006.01) |
| *A61B 5/08* | (2006.01) |
| *A61B 5/11* | (2006.01) |

(52) U.S. Cl.
CPC .............. *A61B 5/0205* (2013.01); *A61B 5/7289* (2013.01); *A61B 7/00* (2013.01); *A61B 5/024* (2013.01); *A61B 5/0816* (2013.01); *A61B 5/1102* (2013.01); *A61B 5/1116* (2013.01); *A61B 5/7264* (2013.01)

(58) Field of Classification Search
CPC ...... A61B 5/024; A61B 5/025; A61B 5/0205; A61B 5/7271; A61B 5/1116; A61B 7/04; A61B 7/003; A61B 2562/0204
USPC .......................................................... 600/528
See application file for complete search history.

(56) References Cited

U.S. PATENT DOCUMENTS

| | | | |
|---|---|---|---|
| 4,446,873 A | * | 5/1984 | Groch .................... A61B 5/024 600/528 |
| 7,174,203 B2 | | 2/2007 | Arand et al. |

(Continued)

OTHER PUBLICATIONS

Weissler, A. M., "Systolic time intervals in heart failure in man", Circulation, 37(2), (Feb. 1968), 149-59.

*Primary Examiner* — Christopher D Koharski
*Assistant Examiner* — Jeremiah Kimball
(74) *Attorney, Agent, or Firm* — Schwegman Lundberg & Woessner, P.A.

(57) ABSTRACT

Heart sound detection systems and methods can use updated heart sound expectation window functions to detect heart sounds. In an example, an initial heart sound expectation window function that describes a heart sound timing can be a function of a physiologic variable such as heart rate, intrinsic vs. non-intrinsic beat, respiration rate, index of circadian timing, or posture. The function can include at least one characteristic parameter that describes a value of the heart sound timing at a specified value of the physiologic variable. In an example, information about a patient heart sound can be detected and used to update a characteristic parameter of an initial heart sound expectation window function, and an updated heart sound expectation window function can be provided using the updated characteristic parameter.

20 Claims, 11 Drawing Sheets

(56) References Cited

U.S. PATENT DOCUMENTS

| | | |
|---|---|---|
| 7,662,104 B2 | 2/2010 | Siejko et al. |
| 7,682,316 B2 | 3/2010 | Anderson et al. |
| 7,853,327 B2 | 12/2010 | Patangay et al. |
| 2003/0163058 A1* | 8/2003 | Osypka et al. ............ 600/513 |
| 2004/0106960 A1* | 6/2004 | Siejko et al. ............. 607/17 |
| 2004/0127792 A1 | 7/2004 | Siejko et al. |
| 2005/0149136 A1* | 7/2005 | Siejko et al. ............. 607/17 |
| 2006/0025699 A1* | 2/2006 | Maile et al. ............. 600/528 |
| 2006/0106322 A1* | 5/2006 | Arand et al. ............. 600/514 |
| 2006/0161070 A1 | 7/2006 | Siejko et al. |
| 2007/0213599 A1* | 9/2007 | Siejko et al. ............. 600/300 |
| 2008/0119749 A1* | 5/2008 | Haro ............. A61B 5/025 600/528 |
| 2008/0119750 A1* | 5/2008 | Patangay et al. ......... 600/528 |
| 2008/0125820 A1 | 5/2008 | Stahmann et al. |
| 2008/0177191 A1* | 7/2008 | Patangay et al. ......... 600/509 |
| 2010/0069768 A1* | 3/2010 | Min et al. ............... 600/528 |
| 2010/0292590 A1* | 11/2010 | Matsukawa ....... A61B 5/02007 600/500 |
| 2011/0190601 A1 | 8/2011 | Osypka et al. |

\* cited by examiner

US 9,375,152 B2

HEART SOUND DETECTION SYSTEMS AND METHODS USING UPDATED HEART SOUND EXPECTATION WINDOW FUNCTIONS

CLAIM OF PRIORITY

This application claims the benefit of priority under 35 U.S.C. §119(e) of An et al., U.S. Provisional Patent Application Ser. No. 61/607,791, entitled "HEART SOUND DETECTION SYSTEMS AND METHODS USING UPDATED HEART SOUND EXPECTATION WINDOW FUNCTIONS", filed on Mar. 7, 2012, which is herein incorporated by reference in its entirety.

BACKGROUND

Mechanical vibrations of a heart can produce heart sounds. Heart sounds occur with each cardiac cycle and can be classified according to the activity associated with the vibration. The first heart sound (S1) is the sound made during closure of the mitral and tricuspid valves. The second heart sound (S2) is made by the closure of the aortic and pulmonary valves. The third heart sound (S3) and fourth heart sound (S4) are often related to abnormal filling pressures of the left ventricle during diastole. Heart sounds can be useful indications of cardiac function status.

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices can be used to treat patients using electrical therapy or to aid a physician or caregiver in patient diagnosis through monitoring of a patient condition, or both. The devices can include or can be connected to electrodes in communication with circuitry to monitor electrical heart activity, or can include one or more sensors to monitor patient physiologic parameters.

Various systems and methods for sensing heart sounds using implantable medical devices have been proposed. For example, Stahmann et al., in U.S. Patent Application Publication No. 2008/0125820, titled "Adaptive Sampling of Heart Sounds," refers to sensing heart sounds according to one or more parameters and altering the one or more parameters using a triggering event.

OVERVIEW

The present inventors have recognized, among other things, that a problem to be solved can include providing an accurate heart sound expectation window that can be used to detect heart sounds. In an example, the present subject matter can provide a solution to this problem, such as by using patient-specific or population-specific heart sound information to provide or update a heart sound expectation window function.

Heart sound detection systems and methods can use updated heart sound expectation window functions to detect one or more types of heart sounds. In an example, an initial heart sound expectation window function that describes a heart sound timing can be a function of a physiologic variable such as heart rate, intrinsic vs. non-intrinsic beat, respiration rate, index of circadian timing, or posture. The function can include at least one characteristic parameter that describes a value of the heart sound timing at a specified value of the physiologic variable. In an example, information about a patient heart sound can be detected and used to update a characteristic parameter of an initial heart sound expectation window function. An updated heart sound expectation window function can be provided using the updated characteristic parameter.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
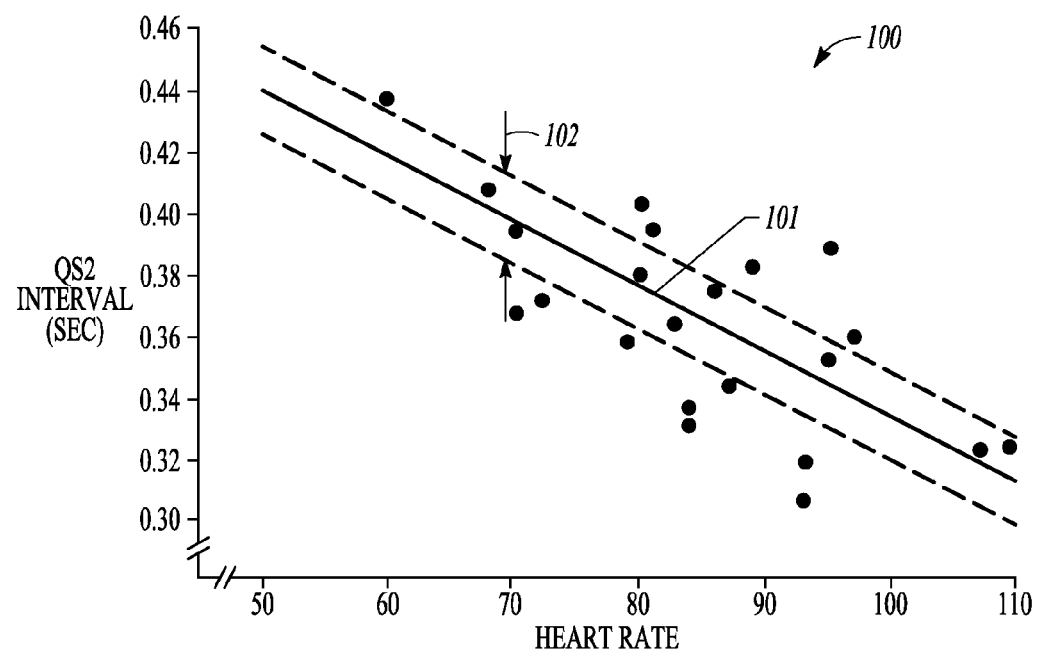
FIG. 1 illustrates generally an example of a linear relationship between heart rate and a heart sound interval.

FIG. 1 illustrates generally an example of a chart 100 that shows a linear relationship between a duration of electromechanical systole and heart rate. This relationship was proposed by Weissler et al., in "Systolic Time Intervals in Heart Failure in Man," *Circulation* 1968; 37: 149-159, which is hereby incorporated herein by reference in its entirety. Weissler et al. defined electromechanical systole, or QS2, as an interval measured from an onset of a QRS complex to a first, high frequency vibration of the aortic component of the second heart sound (S2). Using heart rate as a variable, Weissler et al. empirically determined a linear equation that predicts QS2 (in seconds):

$$QS2=-0.0021(HR)+0.546 \quad (1)$$

In Equation (1), HR is a heart rate calculated as 60/(average R-R interval). Weissler et al. concluded that this inverse relationship between the duration of electromechanical systole and heart rate is due to a shortening of left ventricular ejection time.

Equation (1) is illustrated graphically in FIG. 1 as a Weissler regression line 101 that is based on empirical patient data collected by Weissler et al. The data points illustrate the heart rate and QS2 interval relationships observed by Weissler et al. The dashed lines in FIG. 1 illustrate +/−1 standard deviation ($\sigma$) from the Weissler regression line 101. A QS2 expectation window 102, such as corresponding to a particular heart rate or a range of heart rates, can be established. In an example, the QS2 expectation window 102 can correspond to the +/−1 standard deviation ($\sigma$) from the Weissler regression line 101 at a specified heart rate.

In the example of FIG. 1, the particular QS2 expectation window 102 can be used to predict a timing of an S2 heart sound at about 70 beats per minute (bpm). The central value of the QS2 expectation window 102 at 70 bpm can be calculated as:

$$QS2_{70}=-0.0021(70)+0.546=0.399 \text{ sec}, \quad (2)$$

and the extents of the $QS2_{70}$ expectation window 102 can be calculated as:

$$QS2_{70}+/-\sigma=0.399+/-0.014=0.385 \text{ to } 0.413 \text{ sec}. \quad (3)$$

Thus, using the relationship proposed by Weissler et al., an S2 heart sound can be expected to occur between about 0.385 and 0.413 seconds from an initial onset of a corresponding QRS complex, such as when a patient heart rate is about 70 bpm.

Weissler et al. thus proposed a "one-size-fits-all" approach to identifying an S2 heart sound expectation window. However, additional evidence suggests that this approach is insufficient for predicting reliable, accurate heart sound expectation windows in multiple patient populations.

Figure 2:
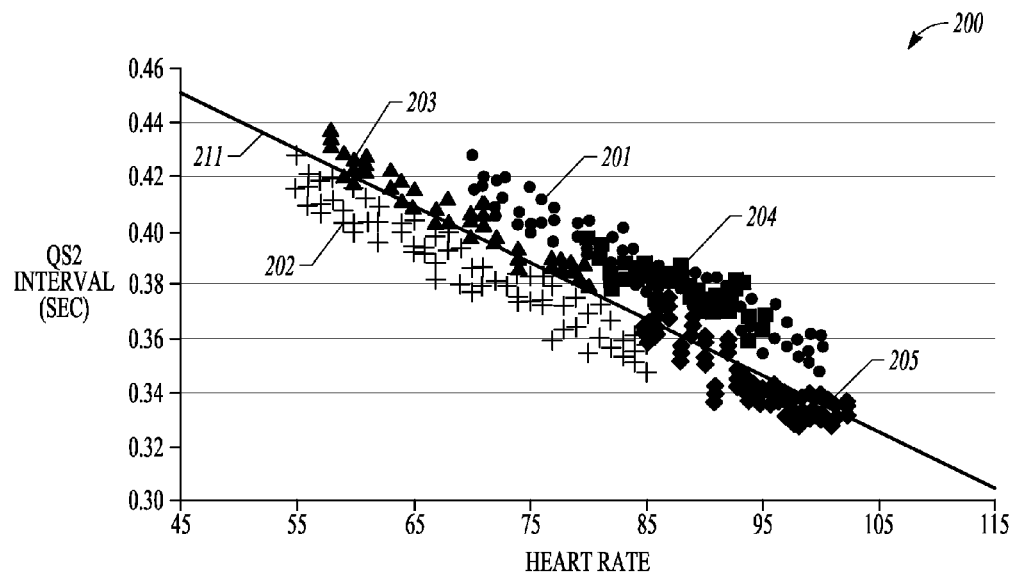
FIG. 2 illustrates generally an example of multiple relationships between heart rate and a heart sound interval.

FIG. 2 illustrates generally an example 200 of multiple relationships between patient heart rate and patient QS2 interval. The example 200 includes multiple conceptualized data points that illustrate particular relationships between QS2 interval and heart rate. The example 200 also includes a composite regression line 211 corresponding to the multiple conceptualized data points. In an example, each set of data points illustrated in FIG. 2 with a common shape can be considered a data cluster. In an example, the individual data clusters can correspond to individual patients. For example, data cluster 201 (e.g., illustrated in FIG. 2 using circles) can correspond to a first patient, data cluster 202 (e.g., illustrated in FIG. 2 using cross-marks) can correspond to a second patient, and so on.

In an example, each conceptualized data cluster illustrated in FIG. 2 can correspond to a particular patient population. A patient population can include a group of patients who share a physiologic attribute, such as a heart rate or heart rate range, a respiration rate or range, an index of circadian timing, a posture status, or a cardiac activity status (e.g., intrinsic cardiac activity or non-intrinsic cardiac activity), among other physiologic attributes. In an example, data cluster 203 (e.g., illustrated in FIG. 2 using triangles) can correspond to one or more patients having a first index of circadian timing, data cluster 204 (e.g., illustrated in FIG. 2 using squares) can correspond to one or more patients having a different second index of circadian timing, and so on.

In an example, data corresponding to any population, such as the data from one or more of the data clusters 201, 202, 203, 204, or 205, can be combined in whole or in part. The combined data can be analyzed, and a corresponding composite regression line can be provided. For example, the composite regression line 211 can correspond to an aggregate population, such as including all of the data points illustrated in the example of FIG. 2 (e.g., including data from all of the data clusters 201, 202, 203, 204, and 205).

Figure 3:
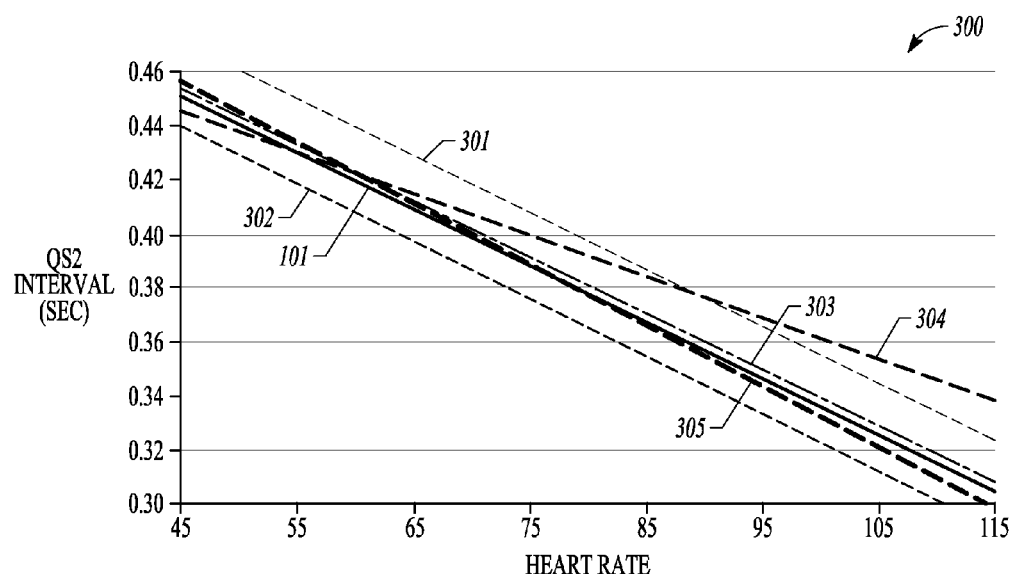
FIG. 3 illustrates generally an example of multiple regression lines that can describe relationships between heart rate and a heart sound interval.

FIG. 3 illustrates generally an example 300 of multiple regression lines that can correspond to various data clusters, such as the data clusters illustrated in FIG. 2. In an example, each data cluster in FIG. 2 can correspond to a different patient, and a unique regression line can be determined for each of the clusters (e.g., for each patient). For example, the data cluster 201 can include information about a first patient's heart rate and corresponding QS2 interval. Using information from the data cluster 201, a regression line 301 can be determined. Similarly, a regression line 302 can be determined using information from the data cluster 202, a regression line 303 can be determined using information from the data cluster 203, and so on. FIG. 3 illustrates generally several regression lines 301, 302, 303, 304, and 305, such as corresponding to the data clusters illustrated in FIG. 2, and the Weissler regression line 101.

In the example of FIG. 2, the Weissler regression line 101 can appear to be an approximate fit to the overall distribution of the data clusters 201, 202, 203, 204, and 205. However, as shown in the example of FIG. 3, regression lines corresponding to each patient population can have different slopes or different intercepts than the Weissler regression line 101. Thus, a heart sound expectation window function generated using Equation (1) or the Weissler regression line 101 can be improved to more accurately predict heart sound timing for individual patients or groups of similarly situated patients. An improved heart sound expectation window function can be provided using patient-specific or patient population-specific information, such as using actual patient data.

Figure 4:
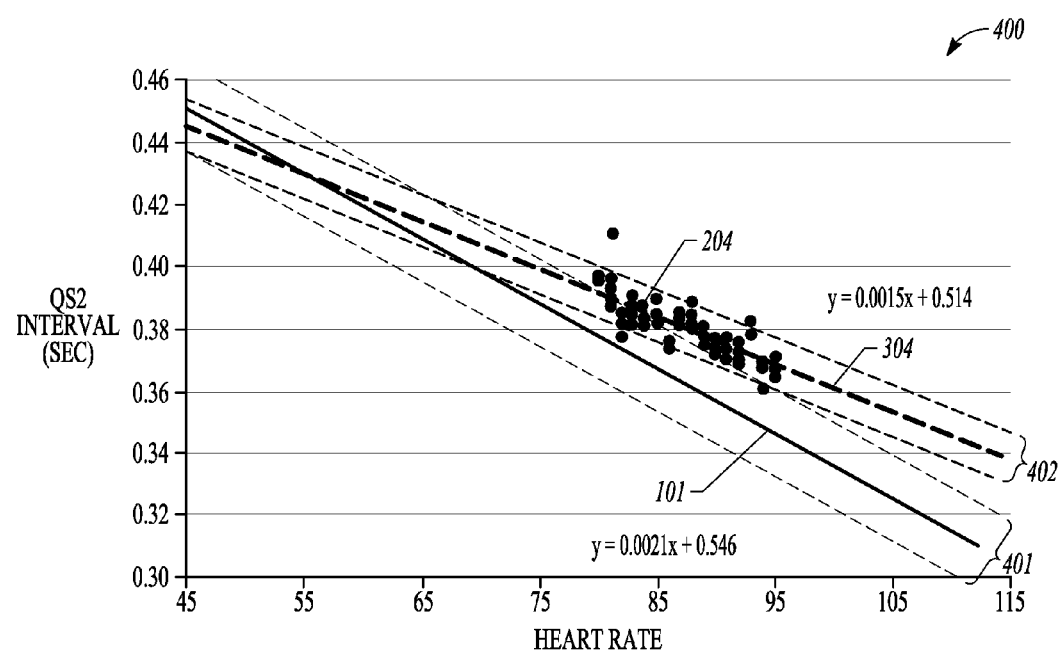
FIG. 4 illustrates generally an example of two different heart sound expectation windows.

FIG. 4 illustrates generally an example of two different heart sound expectation windows. In an example, a first heart sound expectation window 401 can be provided, such as using the Weissler regression line 101. The Weissler regression line 101 can be characterized by one or more characteristic parameters, such as including a slope characteristic parameter (e.g., about −0.0021) and an intercept characteristic parameter (e.g., about 0.546). An upper limit of the first heart sound expectation window 401 can be provided using the Weissler regression line 101+$\sigma$, and a lower limit of the first heart sound expectation window 401 can be provided using the Weissler regression line 101−$\sigma$, such as described above in the discussion of FIG. 1.

In an example, a second heart sound expectation window 402 can be provided, such as using the regression line 304 that corresponds to the conceptualized data cluster 204 (see, e.g., FIGS. 2 and 3). The regression line 304 can be characterized by one or more characteristic parameters, such as including a slope characteristic parameter (e.g., about −0.0015) and an intercept characteristic parameter (e.g., about 0.514). The upper and lower limits of the second heart sound expectation window 402 can be provided using the regression line 304+$\sigma_{304}$, and using the regression line 304−$\sigma_{304}$, respectively, where $\sigma_{304}$ is the standard deviation calculated using the information in the data cluster 204. In an example, $\sigma$ and $\sigma_{304}$ can be differently valued, such as according to the distribution of the data on which the respective regression lines are based. In the example of FIG. 4, σ is about 0.0014, and $\sigma_{304}$ is about 0.0085.

In an example, the first and second heart sound expectation windows 401 and 402 can overlap over a portion, or none, of the heart rate spectrum. Thus, at least over portions of the heart rate spectrum where the heart sound expectation windows do not overlap, a heart sound timing of a patient or patient population that corresponds to the regression line 304 can be more accurately determined using the second heart sound expectation window 402.

Figure 5:
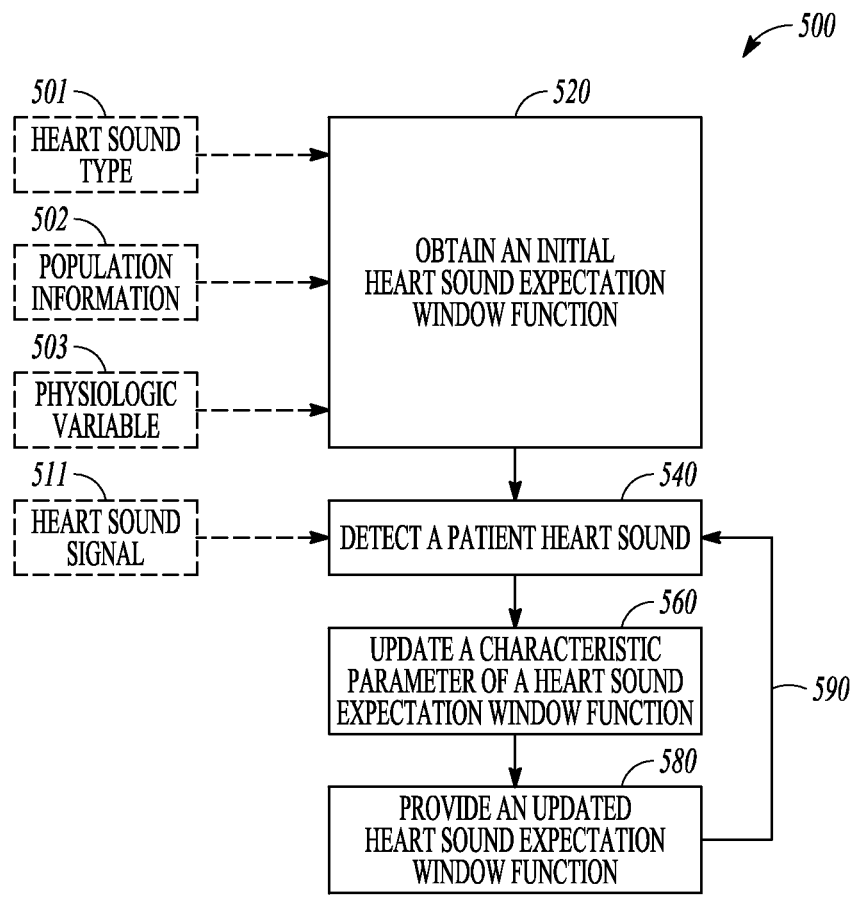
FIG. 5 illustrates generally an example that can include obtaining an initial heart sound expectation window function or providing an updated heart sound expectation window function.

In an example, a heart sound expectation window can be a function of one or more physiologic variables. Various systems and methods can be used to obtain or update a heart sound expectation window function. For example, FIG. 5 illustrates generally an example 500 that can include obtaining an initial heart sound expectation window function or providing an updated heart sound expectation window function.

At 520, an initial heart sound expectation window function, such as corresponding to a specified heart sound type 501, can be obtained. For example, where the heart sound type 501 is an S2 heart sound, the initial heart sound expectation window function can be an initial S2 expectation window function, such as can be optimized to provide information about an expected S2 timing. In an example, the initial heart sound expectation window function can be any of an initial S1, S2, S3, or S4 expectation window function, and any one or more of the initial S1, S2, S3, or S4 expectation window functions can be different functions, such as can be separately and individually optimized to provide information about an expected heart sound timing for the specified type of heart sound. In an example, the initial heart sound expectation window function can be optimized to provide timing information about more than one type of heart sound. For example, a piecewise heart sound expectation window function can be used to provide timing information about S1 and S2 expectation windows.

At 520, an initial heart sound expectation window function can be obtained using population information 502. In an example, different initial heart sound expectation window functions can correspond to different populations. The population information 502 can include information that can be used to distinguish a patient or group of patients from a larger group of patients. For example, a first population can include one or more members who exhibit a particular trait or characteristic. For example, the first population can include patients affected by a particular disease, such as a population of diabetic patients or a population of heart failure patients. A second population can include patients living in a particular geographical area, or a third population can include patients of a specified age or age range. In an example, at 520, an initial heart sound expectation window function can be obtained according to the population information 502, such as where the population information 502 includes several age ranges. For example, one initial heart sound expectation window function can correspond to patients of a first specified age range, and a different second initial heart sound expectation window function can correspond to patients of a different second specified age range. Many other population classifications can be used as well.

Individual members of a particular population can be included in more than one population. For example, a member of a heart failure patient population can also be a member of a particular geographical population. In an example, at 520, multiple initial heart sound expectation window functions can be obtained for a patient belonging to more than one population, and the multiple initial heart sound expectation window functions can be combined to form a single, patient-specific initial heart sound expectation window function.

In an example, one or more physiologic attributes can be used to classify a patient or group of patients into a particular population. Physiologic attributes that can be used to classify a patient or group of patients can include, among others, a heart rate, a respiration rate, an index of circadian timing, a posture status, or a cardiac activity status (e.g., intrinsic cardiac activity or non-intrinsic cardiac activity). For example, a population can include patients in a first posture (e.g., right supine), and a different population can include patients in a second posture (e.g., left supine).

In an example, the initial heart sound expectation window function acquired at 520 can be a function of one or more physiologic variables 503. A physiologic variable can include, among others, a heart rate, a respiration rate, an index of circadian timing, a posture status, or a cardiac activity status (e.g., intrinsic cardiac activity or non-intrinsic cardiac activity). In an example, the initial heart sound expectation window function can be a function of heart rate, such as illustrated in the example of FIG. 4.

In an example, the initial heart sound expectation window function can provide, for a particular physiologic variable input, a heart sound expectation window output that corresponds to the value of the physiologic variable. In an example, the heart sound expectation window output can include multiple timing values, such as a range of timing values, or can be single-valued. In an example, a single-valued output of the function can be used to generate an expectation window. For example, the function output can be a central value of an expectation window, or a duration of an expectation window.

In an example, the initial heart sound expectation window function obtained at 520 can be a linear function. For example, the initial heart sound expectation window function can be a linear function represented by one or more of the regression lines 301, 302, 303, 304, or 305. In an example, the initial heart sound expectation window function can be a function represented by the Weissler regression line 101, or the composite regression line 211. In an example, the initial heart sound expectation window function can be an average of multiple window functions, such as corresponding to one or more patient populations.

In an example, the initial heart sound expectation window function obtained at 520 can be characterized by at least one characteristic parameter that can be used to describe a value of a heart sound timing, or heart sound window, at a specified value of a physiologic variable. For example, where the initial heart sound expectation window function is a linear function (e.g., of the form y=mx+b), the function can be characterized by a characteristic slope parameter (m) or a characteristic intercept parameter (b). In an example, the initial heart sound expectation window function can be a quadratic function (e.g., of the form $y=cx^2+dx+f$) characterized by multiple characteristic coefficients (e.g., c, d, or f). In an example, the initial heart sound expectation window function can be a power function (e.g., of the form $y=gx^j$) characterized by a characteristic coefficient (g) or a characteristic exponent (j). In an example, the initial heart sound expectation window function can be a series function, such as a power series function (e.g., of the form $y=g_j x^j$ for j=0 to j=n) characterized by multiple characteristic coefficients ($g_j$) and a range of a characteristic exponent (j). Other functions having characteristic parameters can also be used.

At 540, a patient heart sound can be detected, such as using the initial heart sound expectation window function. The heart sound can be detected using a heart sound signal 511, such as can be provided using one or more physiologic sensors, such as described below in the example of FIG. 12. In an example, the initial heart sound expectation window function can provide a time window during which a particular type of heart sound can be expected to occur. For example, as described above in the discussion of FIG. 1, an S2 heart sound expectation window can be determined using the QS2 expectation window 102. At about 70 bpm, the QS2 expectation window can begin at about 0.385 seconds after an onset of a particular QRS complex, and can terminate at about 0.413 seconds after the onset of the particular QRS complex. Thus, an S2 heart sound can be expected to occur between about 0.385 and 0.413 seconds after the onset of the particular QRS complex.

At 560, a characteristic parameter of a heart sound expectation window function can be updated, such as using information about a patient heart sound. For example, a characteristic parameter can be updated using information about a patient heart sound detected at 540. Timing, intensity, waveform shape, or other information about a detected patient heart sound, or group of heart sounds, can be used. In an example, an initial heart sound expectation window function can be used to obtain a first set of heart sound data (e.g., including timing information about one or more heart sounds). The first set of heart sound data can be analyzed for fit relative to the initial heart sound expectation window function (e.g., using a correlation coefficient r). In an example, one or more characteristic parameters of the initial heart sound expectation window function can be updated using the first set of heart sound data or the correlation coefficient.

At 580, an updated heart sound expectation window function can be provided, such as using an updated characteristic parameter. For example, the initial heart sound expectation window function obtained at 520 can include a linear function having characteristic intercept or slope parameters. Using information from one or more patient heart sounds (e.g., detected at 540), one or more of the characteristic intercept or slope parameters can be updated. At 580, an updated heart sound expectation window function can be provided using the updated characteristic intercept or slope parameters. At 590, the updated heart sound expectation window function can be used to detect one or more subsequent patient heart sounds.

Referring now to FIGS. 4 and 5, the first heart sound expectation window 401 can be determined using an initial heart sound expectation window function (e.g., obtained at 520). The first heart sound expectation window 401 can be characterized by, among other things, a characteristic intercept parameter (e.g., about 0.546), or a characteristic slope parameter (e.g., about −0.0021) of the initial heart sound expectation window function. At 540, one or more heart sounds can be detected. Timing information from the detected heart sounds can be used to form the data cluster 204, such as using information about a physiologic parameter (e.g., heart rate). The data cluster 204 can represent heart sound data from a particular patient population, such as comprising one or more patients. In an example, all or a portion of the data cluster 204 can fall outside of the first heart sound expectation window 401, such as indicating a need for an updated heart sound expectation window function. At 560, one or more characteristic parameters of the initial heart sound expectation window function can be updated, and at 580, an updated heart sound expectation window function can be provided. For example, the data cluster 204 can be analyzed using a linear regression model. A regression line 304, corresponding to the data cluster 204, can be provided. The regression line 304 can be used to provide an updated heart sound expectation window function, such as can be used to provide the second heart sound expectation window 402. In an example, the updated heart sound expectation window function can include an updated characteristic intercept parameter (e.g., about 0.514) or an updated characteristic slope parameter (e.g., about −0.0015).

Figure 6:
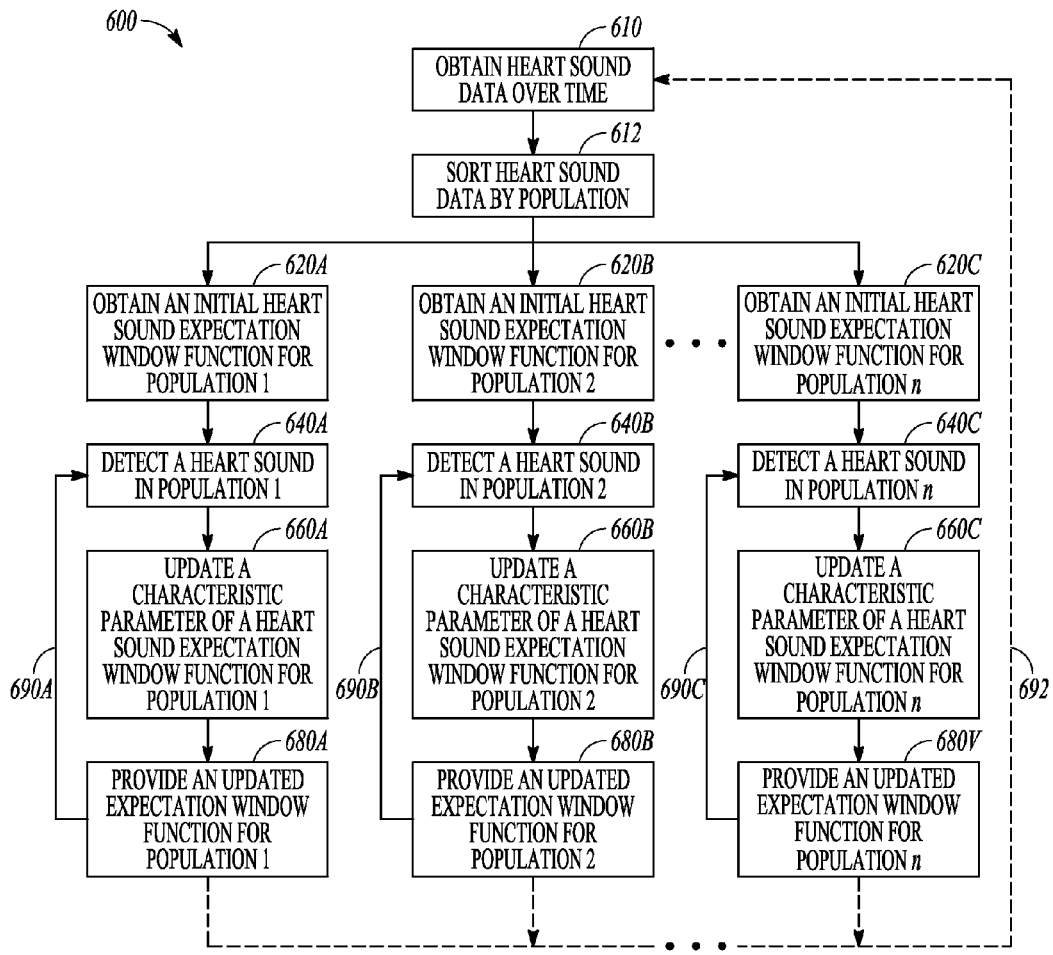
FIG. 6 illustrates generally an example that can include providing multiple, population-specific heart sound expectation window functions.

FIG. 6 illustrates generally an example 600 that can include providing multiple, population-specific heart sound expectation window functions. In an example, at 610, heart sound data can be obtained over time, such as including heart sound data that corresponds to one or more patients. The heart sound data can include information about a heart sound timing and a corresponding physiologic variable, such as heart rate. For example, corresponding heart rate and QS2 interval information can be collected from multiple patients.

At 612, heart sound data can be sorted by population. Referring to FIG. 2, the illustrated data points can represent the heart sound data obtained at 610, and the clustered data (e.g., including the data clusters 201, 202, 203, 204, or 205) can represent the heart sound data sorted by population. As described above, the data cluster 201 can correspond to a first population, the data cluster 202 can correspond to a second population, and so on. In an example, at 612, the heart sound data obtained at 610 can be sorted into n populations. In the example of FIG. 6, at 612, the heart sound data can be sorted into Population 1 (e.g., corresponding to the data cluster 201), Population 2 (e.g., corresponding to the data cluster 202), or Population n (e.g., corresponding to an $n^{th}$ data cluster).

At 620a, a population-specific, initial heart sound expectation window function can be obtained. For example, an initial heart sound expectation window function corresponding to Population 1 can be obtained according to the discussion of FIG. 5 at 520, such as where the population information 502 indicates Population 1. In an example, the initial heart sound expectation window function corresponding to Population 1 can be characterized by a first set of one or more characteristic parameters.

One or more additional, population-specific, initial heart sound expectation window functions can be similarly obtained. For example, at 620b, an initial heart sound expectation window function corresponding to Population 2 (e.g., a different population than Population 1) can be obtained, or at 620c an initial heart sound expectation window function corresponding to Population n can be obtained. As at 620a, each of the functions obtained at 620b or 620c can be obtained according to the discussion of FIG. 5 at 520. In an example, one or more of the functions obtained at 620a, 620b, or 620c, can be the same or different than the other functions. For example, at 620a and 620b, the initial heart sound expectation window functions can correspond to different heart sound types, different patient populations, or different physiologic variables. In an example, each of the initial functions obtained at 620a, 620b, or 620c, can be characterized by at least one unique characteristic parameter or set of characteristic parameters. For example, where the initial functions obtained at 620a, 620b, or 620c, are linear functions, each function can be characterized by a unique characteristic slope parameter (e.g., $m_a$, $m_b$, or $m_c$).

At 640a, a heart sound can be detected for a patient member of Population 1, such as using the initial heart sound expectation window function for Population 1 (e.g., obtained at 620a). Similarly, a heart sound can be detected at 640b for a patient member of Population 2, or at 640c for a patient member of Population n, such as using a corresponding initial heart sound expectation window function (e.g., obtained at 620b or 620c). A heart sound detected at 640a, 640b, or 640c, can be detected according to the discussion of FIG. 5 at 540.

At 660a, 660b, or 660c, a characteristic parameter of a population-specific heart sound expectation window function can be updated, such as according to the discussion of FIG. 5 at 560. For example, where the initial, population-specific functions obtained at 620a, 620b, or 620c, are linear functions, each function can include a characteristic slope parameter (e.g., $m_a$, $m_b$, or $m_c$), among other characteristic parameters. In an example, one or more of the characteristic slope parameters can be updated, such as at 660a, 660b, or 660c, such as using information from one or more of the heart sounds detected at 640a, 640b, or 640c, respectively.

At 680a, 680b, or 680c, an updated, population-specific heart sound expectation window function can be provided, such as according to the discussion of FIG. 5 at 580. For example, at 680a, one or more updated characteristic parameters determined at 660a can be used to provide an updated heart sound expectation window function that corresponds to Population 1. Similarly, at 680b and 680c, one or more updated characteristic parameters determined at 660b and 660c, respectively, can be used to provide updated heart sound expectation window functions for Population 2 and Population n. At 690a, 690b, or 690c, the population-specific, updated heart sound expectation window functions can be used to detect one or more subsequent patient heart sounds, such as corresponding to the same population.

At 692, detected heart sound information, such as across multiple populations, can be obtained over time and fed back into the example 600 at 610. Patient distribution among the various populations can be monitored, assessed, or changed. For example, a first patient can be characterized as belonging to Population 1 at an initial time. However, after a specified assessment period (e.g., one day, or one month, etc.), the patient can be better characterized as belonging to Population 2, such as due to progression of a disease. Accordingly, for subsequent detection of the patient's heart sounds, a heart sound expectation window function corresponding to Population 2 can be used.

In an example, the steps 620a, 640a, 660a, 680a, or 690a, can be used to accurately and efficiently track a patient's heart sound timing variation as long as the patient's heart sound timing can be accurately modeled using a function of the same type as is used for Population 1. However, since patient conditions can change, patients can benefit from occasional reassessment of population status. For example, the initial heart sound expectation window function for Population 1 can be a first type of function, such as a linear function characterized by a first set of characteristic parameters. An initial heart sound expectation window function for Population 2 can be a different second type of function, such as a quadratic function characterized by a different second set of characteristic parameters. Thus, as the first patient's heart sound timing becomes less predictable using the heart sound expectation window function for Population 1, the first patient can be reassigned to another population (e.g., Population 2) for subsequent heart sound monitoring.

Figure 7:
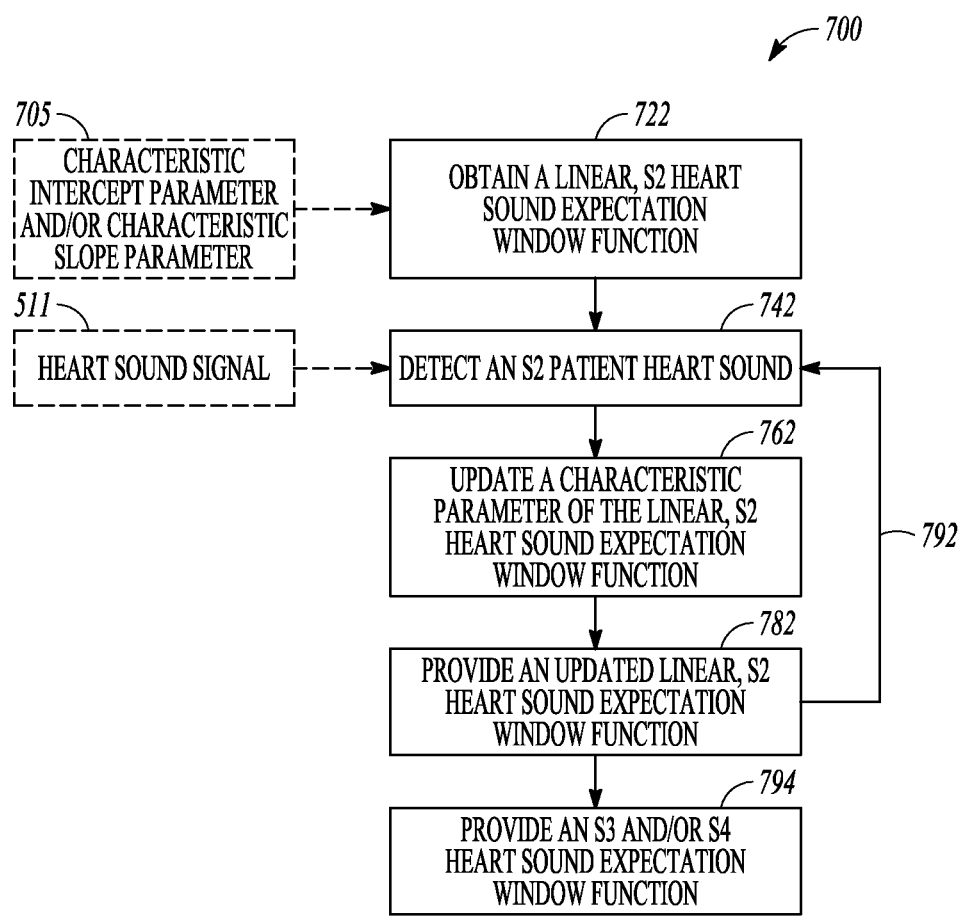
FIG. 7 illustrates generally an example that can include providing heart sound expectation windows for heart sounds of more than one type.
Figure 8:
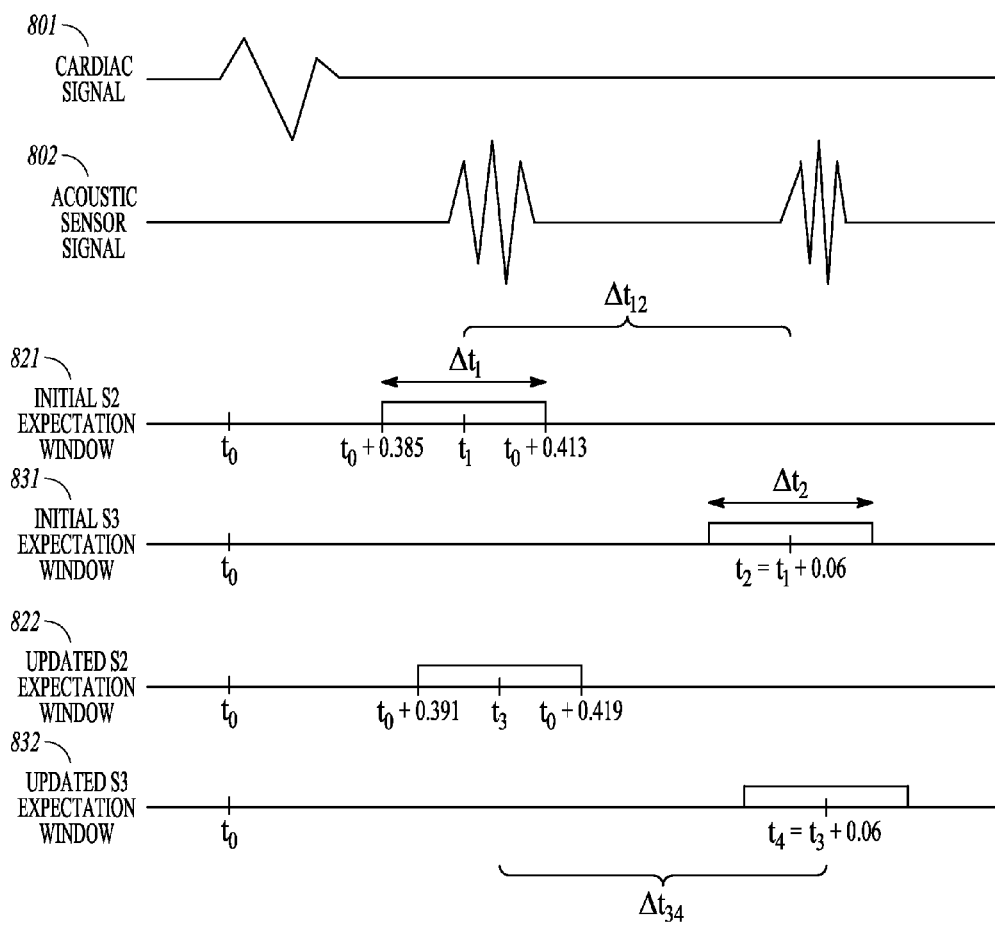
FIG. 8 illustrates generally an example that can include multiple heart sound windows corresponding to different heart sound types.

FIGS. 7 and 8 illustrate generally examples of using an expectation window corresponding to a first heart sound type to provide an additional expectation window corresponding to a second heart sound type. Some heart sounds can be easier to detect than others. For example, an amplitude of an acoustic S2 heart sound signal can be greater than an amplitude of an acoustic S3 heart sound signal. By detecting a heart sound that has a higher signal strength (e.g., an S2 heart sound) using an updated heart sound expectation window, and using a known relationship between that heart sound and a heart sound that has a weaker signal strength, the heart sound with the weaker signal strength can be more accurately detected.

FIG. 7 illustrates generally an example 700 that can include providing heart sound expectation windows for heart sounds of more than one type. At 722, a heart sound expectation window function can be obtained, such as a linear, S2 heart sound expectation window function. One or more characteristic parameters can be used to describe the S2 heart sound expectation window function, such as a characteristic intercept parameter or a characteristic slope parameter 705. In an example, the S2 heart sound expectation window function can be obtained according to the discussion of FIG. 5 at 520, such as where the heart sound type 501 is an S2 heart sound type.

At 742, an S2 patient heart sound can be detected, such as according to the discussion of FIG. 5 at 540. For example, the S2 patient heart sound can be detected using the heart sound signal 511. At 762, a characteristic parameter of the linear, S2 heart sound expectation window function can be updated, such as using information from the S2 patient heart sound detected at 742. For example, the characteristic intercept parameter or the characteristic slope parameter 705 can be updated at 762. At 782, an updated linear, S2 heart sound expectation window function can be provided, such as according to the discussion of FIG. 5 at 580, such as using the updated characteristic parameter(s). In an example, at 792, the updated linear, S2 heart sound expectation window function can be used to detect one or more subsequent patient heart sounds, such as including subsequent S2 heart sounds. In an example, at 792, the updated linear, S2 heart sound expectation window function can be used to refine one or more previously-detected patient heart sounds, such as an S2 heart sound detected at 742. Although the example of FIG. 7 at 722, 742, 762, and 782, is generally configured for use with an S2 heart sound and a linear function, the example could be similarly configured for use with a heart sound or function of a different type, such as with an S1 heart sound or a non-linear function.

In an example, at 794, an additional heart sound expectation window or heart sound expectation window function can be provided, such as using the updated linear, S2 heart sound expectation window function. For example, an S3 or S4 heart sound expectation window, or expectation window function, can be updated using information about an S2 heart sound expectation window or an S2 heart sound expectation window function.

FIG. 8 illustrates generally an example of multiple heart sound windows, such as corresponding to different heart sound types. In the example of FIG. 8, a cardiac signal 801 can be provided, such as can be used to trigger a heart sound timing window. For example, an S2 timing window can be triggered at $t_0$, such as at an onset of a QRS wave determined using the cardiac signal 801. In an example, an acoustic sensor signal 802 can be provided. The acoustic sensor signal 802 can include an indication of acoustic energy, including a heart sound, and can be provided simultaneously with the cardiac signal 801.

In an example, an initial S2 heart sound expectation window 821 (e.g., obtained at 722 in the example of FIG. 7) can have a duration $\Delta t_1$ and a central value at a first time $t_1$. An initial S3 heart sound expectation window 831 can have a duration $\Delta t_2$ and a central value at a subsequent second time $t_2$. The central value at the subsequent second time $t_2$ can be offset from the first time by a duration $\Delta t_{12}$. In an example, the central value of the initial S3 heart sound expectation window 831 can be determined by adding a specified amount to the central value of the initial S2 heart sound expectation window 821. In an example, the specified amount can be a function of a physiologic variable, or can be a constant value. In the example of FIG. 8, the central value of the initial S3 heart sound expectation window 831 can be determined by adding 0.06 seconds to $t_1$.

In an example, an S2 patient heart sound can be detected (e.g., at 742 in the example of FIG. 7) using the acoustic sensor signal 802, and timing information about the heart sound can be determined. The timing information can be used to update a characteristic parameter of an initial S2 expectation window function (e.g., at 762 in the example of FIG. 7), and an updated S2 expectation window function can be provided (e.g., at 782 in the example of FIG. 7). An updated S2 expectation window 822 can be provided using the updated S2 expectation window function. The updated S2 expectation window 822 can have a duration that is the same or different than $\Delta t_1$, and a central value of the updated S2 expectation window 822 can be the same or different than $t_1$. In the example of FIG. 8, the central value of the updated S2 expectation window can be $t_3$. In an example, a duration of the updated S2 expectation window can also be updated, such as by lengthening or shortening the duration.

In the example of FIG. 8, an updated S3 expectation window 832 can be provided (e.g., at 794 in the example of FIG. 7), such as using the updated S2 expectation window 822. In an example, the central value of the updated S3 heart sound expectation window 832 can be determined by adding a specified amount to the central value of the updated S2 heart sound expectation window 822. In an example, the specified amount can be a function of a physiologic variable, or can be a constant value. In the example of FIG. 8, the specified amount to be added to the initial and updated S3 heart sound expectation windows 831 and 832 can be a constant value of about 0.06 seconds. Accordingly, the central value of the updated S3 heart sound expectation window 832 can be about $t_4 = t_3 + 0.06$ seconds. The central values at times $t_3$ and $t_4$ can be offset by a duration of $\Delta t_{34}$. In an example, $\Delta t_{34}$ can be the same as or different than $\Delta t_{12}$.

Figure 9:
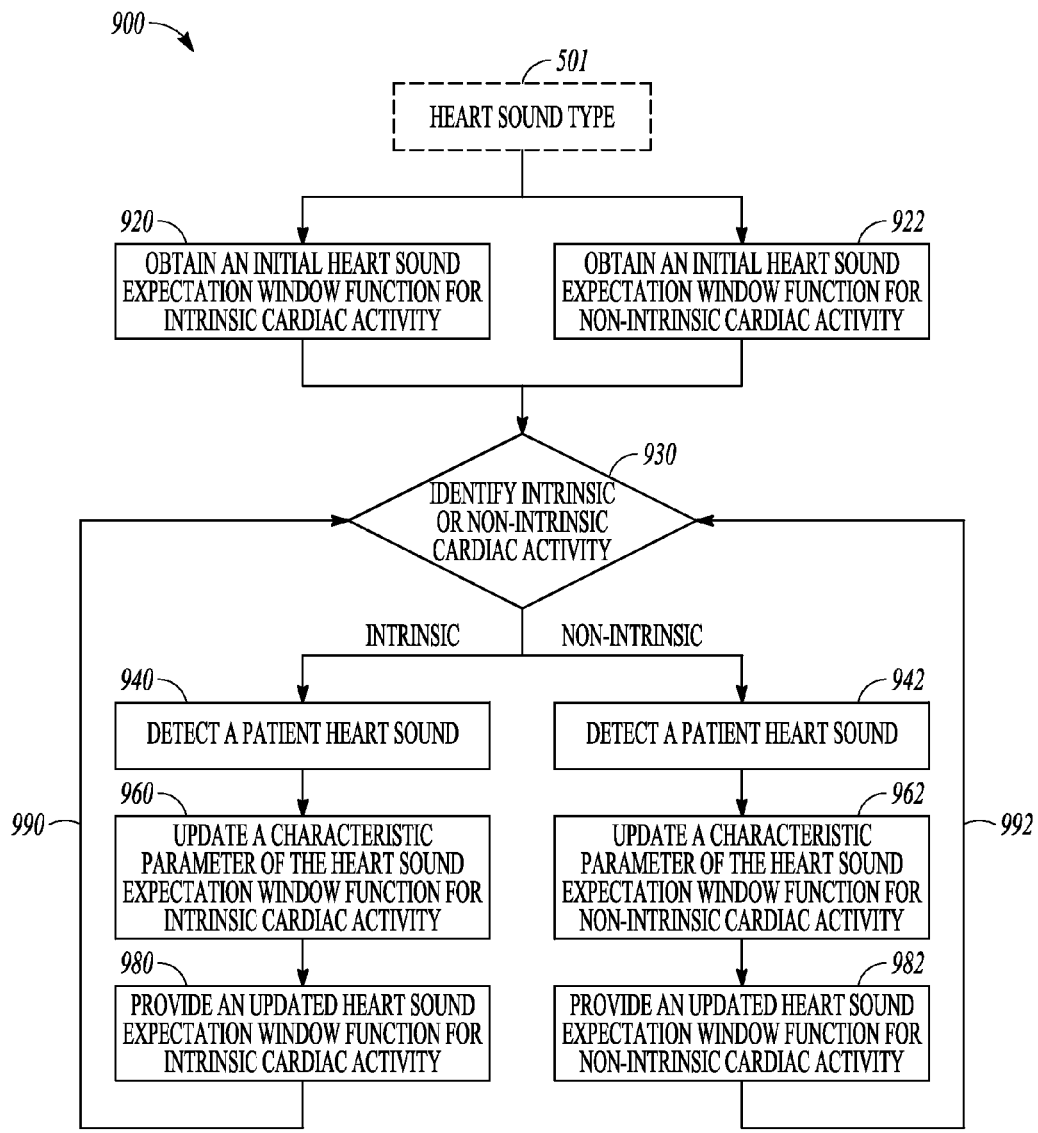
FIG. 9 illustrates generally an example that can include providing a heart sound expectation window function as a function of a cardiac activity status.
Figure 10:
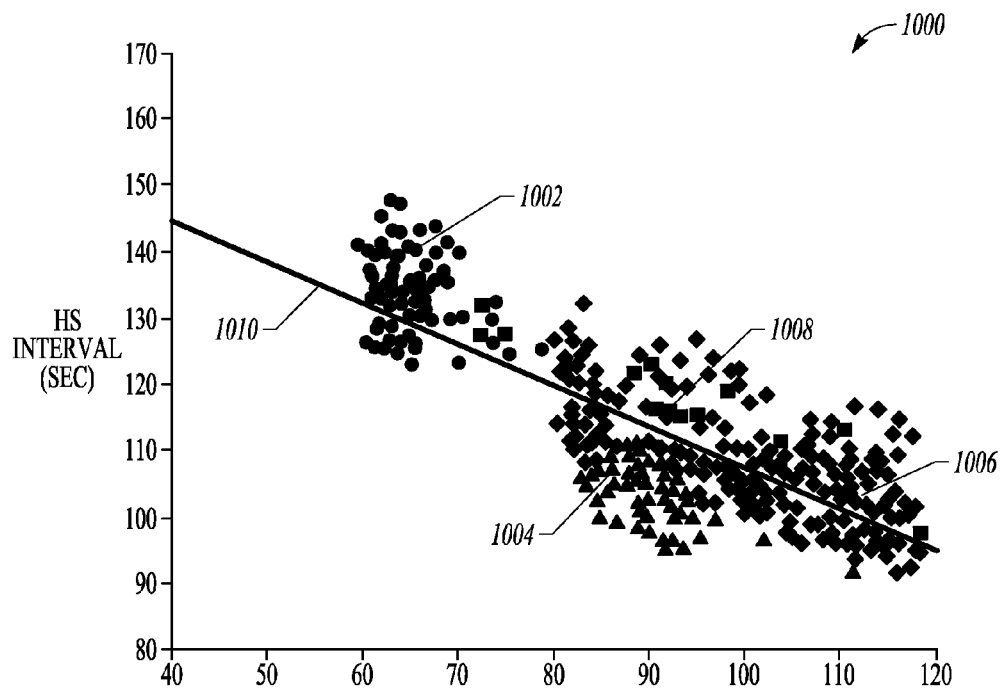
FIG. 10 illustrates generally an example of a heart sound expectation window function that corresponds to intrinsic cardiac activity.
Figure 11:
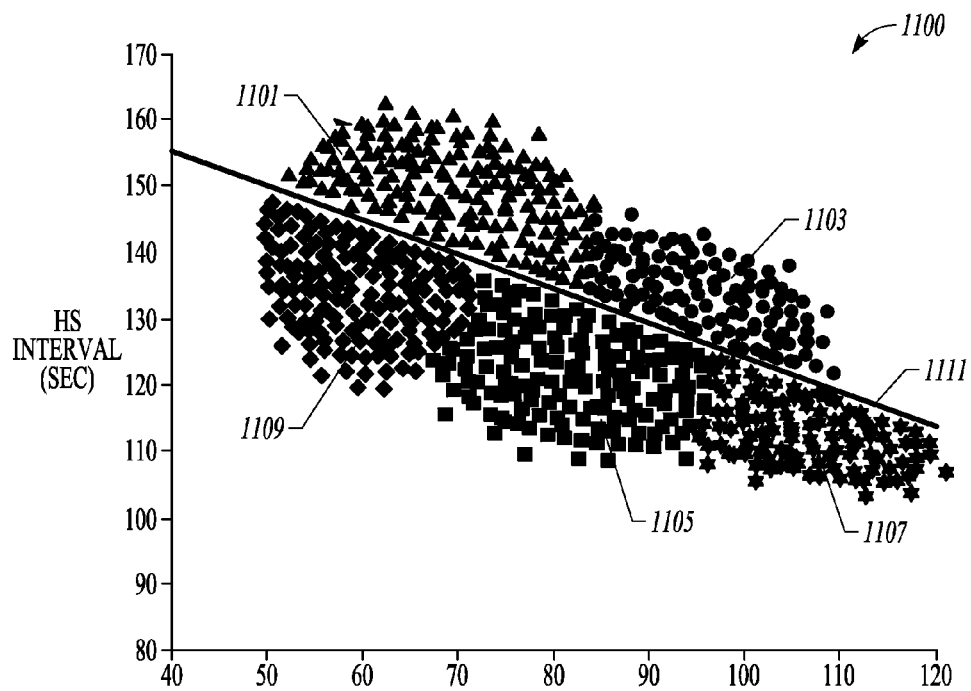
FIG. 11 illustrates generally an example of a heart sound expectation window function that corresponds to non-intrinsic cardiac activity.

As described above in the example of FIG. 5, a heart sound expectation window function can be a function of one or more physiologic variables. For example, a heart sound expectation window function can be a function of cardiac activity status. FIG. 9 illustrates generally an example 900 of providing heart sound expectation window functions that are functions of cardiac activity status. FIG. 10 and FIG. 11 illustrate graphically examples of different heart sound expectation window functions that are each functions of different cardiac activity statuses.

In the example of FIG. 9, at 920, an initial heart sound expectation window function corresponding to intrinsic cardiac activity can be obtained. At 922, an initial heart sound expectation window function corresponding to non-intrinsic cardiac activity can be obtained. In an example, population information 502 or information about a heart sound type 501 can be used to obtain the initial functions at 920 or 922, such as according to the discussion of FIG. 5 at 520.

In an example, the initial heart sound expectation window functions acquired at 920 or 922 can be characterized by at least one characteristic parameter that can be used to describe a value of a heart sound timing at a specified value of a physiologic variable. For example, where the initial heart sound expectation window function corresponding to intrinsic cardiac activity is a linear function (e.g., of the form $y=mx+b$), the function can be characterized by a characteristic slope parameter (m) or a characteristic intercept parameter (b).

At 930, intrinsic or non-intrinsic cardiac activity can be identified. For example, a heart sound signal, cardiac signal, or other signal indicative of cardiac activity can be received and analyzed to determine whether a particular heart beat or portion of a heart beat is intrinsic or non-intrinsic (e.g., paced). In an example, non-intrinsic cardiac activity, such as including a non-intrinsic beat, can be distinguished from intrinsic cardiac activity by analyzing a characteristic of a QRS waveform (e.g., R-wave timing). In an example, intrinsic or non-intrinsic cardiac activity can be identified after detecting a patient heart sound. For example, the timing of S2 in a non-intrinsic beat can be delayed relative to the timing of S2 in an intrinsic beat. Accordingly, in the example of FIG. 9, the identification of intrinsic or non-intrinsic cardiac activity (e.g., at 930) can occur before or after detection of a patient heart sound (e.g., at 940 or 942).

At 940, a patient heart sound can be detected, such as using the initial heart sound expectation window function corresponding to intrinsic cardiac activity. The heart sound can be detected using a heart sound signal 511, such as can be provided using one or more physiological sensors, such as described below in the example of FIG. 12. In an example, the initial heart sound expectation window function corresponding to intrinsic cardiac activity can provide a time window during which a particular type of heart sound can be expected to occur, such as when cardiac function is intrinsic (e.g., not paced). Alternatively, at 942, a patient heart sound can be detected using the initial heart sound expectation window function corresponding to non-intrinsic cardiac activity, such as when non-intrinsic (e.g., paced) cardiac activity is indicated at 930.

If intrinsic cardiac activity is detected at 930, the patient heart sound detected at 940 can be used at 960 to update a characteristic parameter of the heart sound expectation window function corresponding to intrinsic cardiac activity. For example, the characteristic parameter can be updated according to the discussion of FIG. 5 at 560. If non-intrinsic cardiac activity is detected at 930, the patient heart sound detected at 942 can be used at 962 to update a characteristic parameter of the heart sound expectation window function corresponding to non-intrinsic cardiac activity.

At 980, if the cardiac activity detected at 930 is intrinsic, an updated heart sound expectation window function corresponding to intrinsic cardiac activity can be provided. In an example, one or more updated characteristic parameters (e.g., updated at 960) can be used to provide the updated function. The updated function can be provided as described above in the discussion of FIG. 5 at 580. At 982, if the cardiac activity detected at 930 is not intrinsic, an updated heart sound expectation window function corresponding to non-intrinsic cardiac activity can be provided. In an example, one or more updated characteristic parameters (e.g., updated at 962) can be used to provide the updated function.

In an example, at 990, the updated heart sound expectation window function corresponding to intrinsic cardiac activity (e.g., provided at 980) can be used to detect a subsequent heart sound. Subsequent cardiac activity information, such as including subsequent heart sound information, can be received and analyzed to discern whether the cardiac activity is intrinsic or non-intrinsic. When the subsequent cardiac activity information indicates intrinsic activity, the updated heart sound expectation window function corresponding to intrinsic cardiac activity can be used to detect a heart sound. Similarly, at 992, the updated heart sound expectation window function corresponding to non-intrinsic cardiac activity (e.g., provided at 982) can be used to detect a subsequent heart sound when subsequent cardiac activity information indicates non-intrinsic cardiac activity.

FIG. 10 illustrates generally an example 1000 of a heart sound expectation window function 1010 corresponding to intrinsic cardiac activity. The example 1000 includes multiple conceptualized data points that illustrate particular heart sound interval and heart rate relationships, such as corresponding to intrinsic cardiac activity. In an example, a first intrinsic data cluster 1002 can include heart sound interval and heart rate information for a first patient, and a second intrinsic data cluster 1004 can include heart sound interval and heart rate information for a second patient. Third and fourth intrinsic data clusters 1006 and 1008 can similarly include heart sound information for respective third and fourth patients. Additional or fewer data clusters can be used. In an example, the data clusters can represent other populations, such as described above, as long as the populations can also be characterized by intrinsic cardiac activity.

In an example, the heart sound expectation window function 1010 can be derived using multiple data clusters, such as using multiple data clusters corresponding to intrinsic cardiac activity. In the example of FIG. 10, the heart sound expectation window function 1010 can be a linear function. The linear function can have one or more characteristic parameters, such as a characteristic intercept parameter of about 144 ms at 40 bmp, or a characteristic slope parameter of about −0.614.

FIG. 11 illustrates generally an example 1100 of a heart sound expectation window function 1111 corresponding to non-intrinsic cardiac activity. The example 1100 includes multiple conceptualized data points that illustrate particular heart sound interval and heart rate relationships, such as corresponding to non-intrinsic cardiac activity. In an example, a first non-intrinsic data cluster 1001 can include heart sound interval and heart rate information for a first patient, and a second non-intrinsic data cluster 1003 can include heart sound interval and heart rate information for a second patient. Additional non-intrinsic data clusters, such as third, fourth, and fifth data clusters 1005, 1007, and 1009, can similarly include heart sound information for respective patients. Additional or fewer data clusters can be used. In an example, the data clusters can represent other populations, such as described above, as long as the populations can also be characterized by non-intrinsic cardiac activity. In an example, the heart sound expectation window function 1111 can be derived using multiple data clusters, such as data clusters corresponding to non-intrinsic cardiac activity. In the example of FIG. 10, the heart sound expectation window function 1111 can be a linear function, and the linear function can have one or more characteristic parameters, such as a characteristic intercept parameter of about 155 ms at 40 bmp, or a characteristic slope parameter of about −0.533.

In an example, different heart sound expectation window functions can be provided for different cardiac activity statuses, such as shown in FIGS. 10 and 11. In an example, the different heart sound expectation window functions can be functions of the same or a different type (e.g., linear, quadratic, exponential, etc.). In an example, the different heart sound expectation window functions can be characterized by one or more different characteristic parameters. In an example, a characteristic parameter of a function corresponding to a first cardiac activity status can be shared by a function corresponding to a second cardiac activity status.

Figure 12:
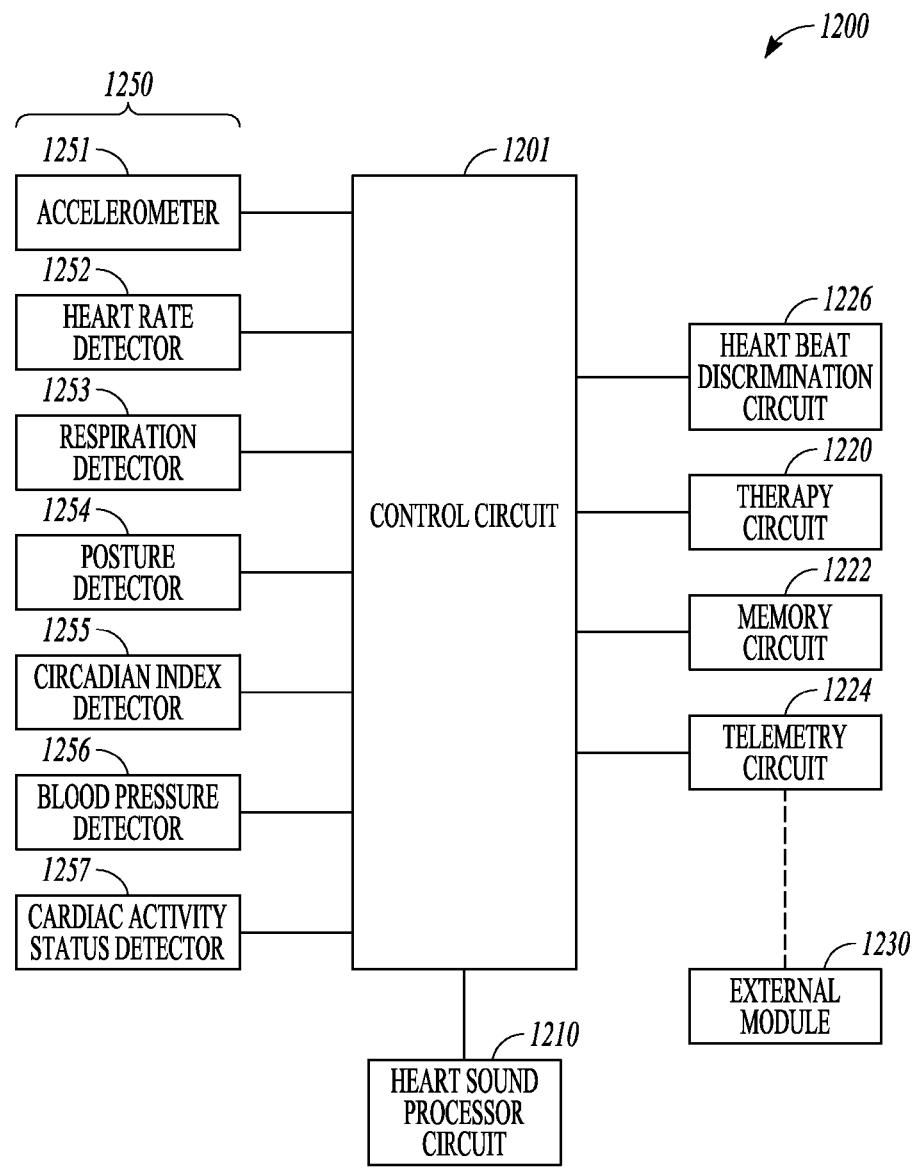
FIG. 12 illustrates generally an example of a heart sound processor circuit, a control circuit, and one or more physiologic sensors.

Various systems can be used to implement the methods, algorithms, or functions described above. For example, FIG. 12 illustrates generally an example of a device 1200, such as an ambulatory or implantable medical device, that can include a control circuit 1201. The control circuit 1201 can be coupled to one or more physiologic sensors 1250 that can be configured to provide a signal indicative of a physiologic variable to the control circuit 1201. In an example, the control circuit 1201 can be coupled to a heart sound processor circuit 1210. The heart sound processor circuit 1210 can receive information from the one or more physiologic sensors 1250, such as via the control circuit 1201, to determine how the device 1200 detects heart sounds. In an example, the one or more physiologic sensors 1250 can be coupled to the control circuit 1201, such as via a wired or wireless connection.

The heart sound processor circuit 1210 can be configured to provide a heart sound expectation window or heart sound expectation window function, such as according to the discussion of FIG. 5 at 520. The heart sound processor circuit 1210 can be configured to detect a patient heart sound, such as according to the discussion of FIG. 5 at 540, such as using information received from the one or more physiologic sensors 1250. In an example, the heart sound processor circuit 1210 or the control circuit 1201 can be configured to update a characteristic parameter of a heart sound expectation window function, such as according to the discussion of FIG. 5 at 560. An updated heart sound expectation window function can be provided by the heart sound processor circuit 1210, such as according to the discussion of FIG. 5 at 580, such as using an updated characteristic parameter.

Examples of the one or more physiologic sensors 1250 can include, among others, an accelerometer 1251, a heart rate detector 1252, a respiration detector 1253, such as including a respiration rate detector or a respiration phase detector, a posture detector 1254, a circadian index detector 1255, such as including a sleep detector, a blood pressure detector 1256, a cardiac activity status detector 1257, or one or more other physiologic sensors. In an example, any one or more of the physiologic sensors 1250 can be included in the device 1200, or can be external to the device 1200.

In an example, an output signal of one or more of the physiologic sensors 1250 can be used to provide the physiologic variable 503 or the population information 502 (see, e.g., the discussion of FIG. 5). For example, one or more of the accelerometer 1251 or the heart rate detector 1252, among other sensors or circuits, can be used to provide the physiologic variable 503 as a heart rate signal, such as can be used to generate a heart sound expectation window function.

In an example, an output signal of one or more of the physiologic circuits or sensors 1250 can be used to provide the population information 502. For example, information from the accelerometer 1251 can be used to provide the population information 502 by detecting a physical activity level. In an example, a population can include patient(s) at a specified physical activity level or range of physical activity levels. In an example, information from the respiration detector 1253 or another sensor or circuit can be used to provide information about a physical activity level.

In an example, the accelerometer 1251 can be coupled to the control circuit 1201. The accelerometer 1251 can be configured to provide a signal representative of, among other information, a patient posture or patient physical activity level. In an example, the accelerometer 1251 can be configured as an acoustic sensor that can detect acoustic vibration information and provide a signal indicative of a patient heart sound (e.g., the acoustic sensor signal 802 or the heart sound signal 511), such as when the accelerometer 1251 is disposed in or near a patient heart. In an example, the heart sound processor circuit 1210 can be provided with information from the accelerometer 1251, and the heart sound processor circuit 1210 can be configured to recognize a particular type of heart sound from the accelerometer signal. Some systems and methods that can be used to recognize or identify a heart sound are described by Patangay et al. in U.S. Pat. No. 7,853, 327, titled "Heart Sound Tracking System and Method,"

which is hereby incorporated herein by reference in its entirety. In an example, acoustic heart sound information can be obtained using a microphone, and an output signal from the microphone can be provided to the heart sound processor circuit 1210 for analysis.

In an example, the heart rate detector 1252 or the respiration detector 1253 can be coupled to the control circuit 1201. The heart rate detector 1252 can be configured to provide a signal representative of a patient heart rate, and the respiration detector 1253 can be configured to provide a signal representative of a patient respiration rate or respiration phase. In an example, an impedance detector can be used to provide an impedance signal, and the heart rate detector 1252 or the respiration detector 1253 can use the impedance signal to provide the signal representative of the patient heart rate or respiration rate or phase. In an example, information from one or both of the heart rate detector 1252 or the respiration detector 1253 can be used to provide the physiologic variable 503 or the population information 502. For example, a heart sound window function can be a function of heart rate, respiration rate, or respiration phase. In an example, a patient population can be determined using groups of patients having similar heart rates, respiration rates, or respiration phases.

In an example, the posture detector 1254 can be coupled to the control circuit 1201. Information from the posture detector 1254 can be used to provide the physiologic variable 503 or the population information 502. For example, particular posture status information from the posture detector 1254 can be used as the physiologic variable 503, and a heart sound window function can be a function of the particular posture status. For example, heart sound interval information for a specified type of heart sound can be correlated with the particular posture status, and a function can be generated. In an example, information from the posture detector 1254 can be used to provide the population information 502. For example, patients can be grouped according to a particular posture or position.

In an example, a heart sound can be measured in correspondence with posture information, such as using posture information received from the posture detector 1254. For example, Siejko et al., in U.S. Pat. No. 7,662,104, titled "Method for Correction of Posture Dependence on Heart Sounds," which is hereby incorporated herein by reference in its entirety, describe adjusting a heart sound measurement using patient posture information.

In an example, the circadian index detector 1255 can be coupled to the control circuit 1201. The circadian index detector 1255 can be used to detect a patient circadian cycle and identify a particular point or portion of the patient circadian cycle. For example, the circadian index detector 1255 can be used to detect a patient sleep/wake cycle, or other time of day information. Information from the circadian index detector 1255 can be used to provide one or both of the physiologic variable 503 or the population information 502. In an example, a heart sound expectation window function can be a function of a particular circadian index (e.g., a function of time of day), or patient(s) can be grouped into one or more populations according to circadian index (e.g., time of day, awake vs. asleep, etc.).

In an example, the blood pressure detector 1256 can be coupled to the control circuit 1201. The blood pressure detector 1256 can be used to detect, among other things, a particular patient blood pressure or a pulsatile signal. Information from the blood pressure detector 1256 can be used to provide the physiologic variable 503 or the population information 502. In an example, a heart sound expectation window function can be a function of blood pressure, such as can be used to correlate a particular blood pressure with a particular heart sound timing. In an example, multiple patient populations can be provided by grouping patients according to a particular blood pressure or range of blood pressures. In an example, a feature of the pulsatile signal (e.g., a peak timing, amplitude, frequency, or other feature) can be used to classify patients into multiple populations, or can be used as a physiologic variable.

In an example, the cardiac activity status detector 1257 can be coupled to the control circuit 1201. The cardiac activity status detector 1257 can be used to detect or determine whether cardiac activity is intrinsic (e.g., cardiac activity that is not paced) or non-intrinsic (e.g., paced cardiac activity). In an example, the cardiac activity status detector 1257 can be used in the example of FIG. 9, at 930, to identify intrinsic or non-intrinsic cardiac activity. Information from the cardiac activity status detector 1257 can be used to provide the physiologic variable 503, such as can be used to provide a heart sound expectation window function. For example, a function can be used to correlate a heart sound timing interval and a particular cardiac activity status. Information from the cardiac activity status detector 1257 can be used to provide the population information 502, such as can be used to classify patients into multiple populations according to cardiac activity status. For example, a first population can include patients experiencing intrinsic cardiac activity, and a second population can include patients experiencing non-intrinsic, or paced, cardiac activity.

In an example, one or more other physiologic sensors or circuits can be used to provide the physiologic variable 503 or the population information 502. For example, a diagnostic circuit or indication (e.g., pre-set by a clinician or automatically provided) can include an identified patient risk factor, such as one or more of a heart failure decompensation risk factor, an increase in an occurrence or intensity of one or more of an S3 heart sound or an S4 heart sound, an occurrence or change in a time-splitting of an S1 heart sound or an S2 heart sound, or a population risk stratifier. A heart failure decompensation risk factor can include one or more of, for example, an increased respiration rate (e.g., detected using the respiration detector 1253), a decreased thoracic impedance (e.g., detected using the respiration detector 1253), or an increased resting heart rate (e.g., detected using the heart rate detector 1252). Similarly, an onset or an increase in the intensity of an S3 or an S4 heart sound can be risk factors, and the manner in which heart sound information is obtained by a device may be altered as a function of the onset or increase in the intensity of the S3 or S4 heart sounds. In an example, an occurrence or change in a splitting of an S1 heart sound or an occurrence or a change in a splitting of an S2 heart sound can be risk factors, and heart sound data acquisition may be adapted accordingly.

In an example, some heart sounds can be detected or processed using a noise suppression algorithm, such as can be applied to a heart sound signal during particular heart sound expectation windows. To conserve battery life, such as in an implantable medical device, the noise suppression algorithm can be turned off during time periods outside of the particular heart sound expectation window. In an example, the control circuit 1201 or the heart sound processor circuit 1210 can control such additional processing.

In the example of FIG. 12, the device 1200 can include a therapy circuit 1220. The therapy circuit 1220 can be coupled to the control circuit 1201 and can be configured to provide one or more of pacing, defibrillation, cardioversion, cardiac resynchronization, and neural stimulation therapy, such as using information from the heart sound processor circuit 1210 or the control circuit 1201. The device 1200 can include a telemetry circuit 1224, such as coupled to the control circuit 1201. The telemetry circuit 1224 can wirelessly communicatively couple the device 1200 to one or more adjunct or external modules 1230. In an example, the telemetry circuit 1224 can transmit heart sound information, or heart sound expectation window function information, to the external module 1230.

In an example, the device 1200 can include a memory circuit 1222, such as can be used to store information about a heart sound, a heart sound signal, or information about a signal provided by one or more of the physiologic sensors 1250. In an example, the memory circuit 1222 can store a heart sound signal and information about one or more physiologic variables and, after a specified period of time, the heart sound processor circuit 1210 can use the stored heart sound signal and other information to identify or update a heart sound expectation window function. In an example, some or all of the information about the heart sound signal or physiologic variables can be stored externally to the device 1200, such as using the external module 1230.

Figure 13:
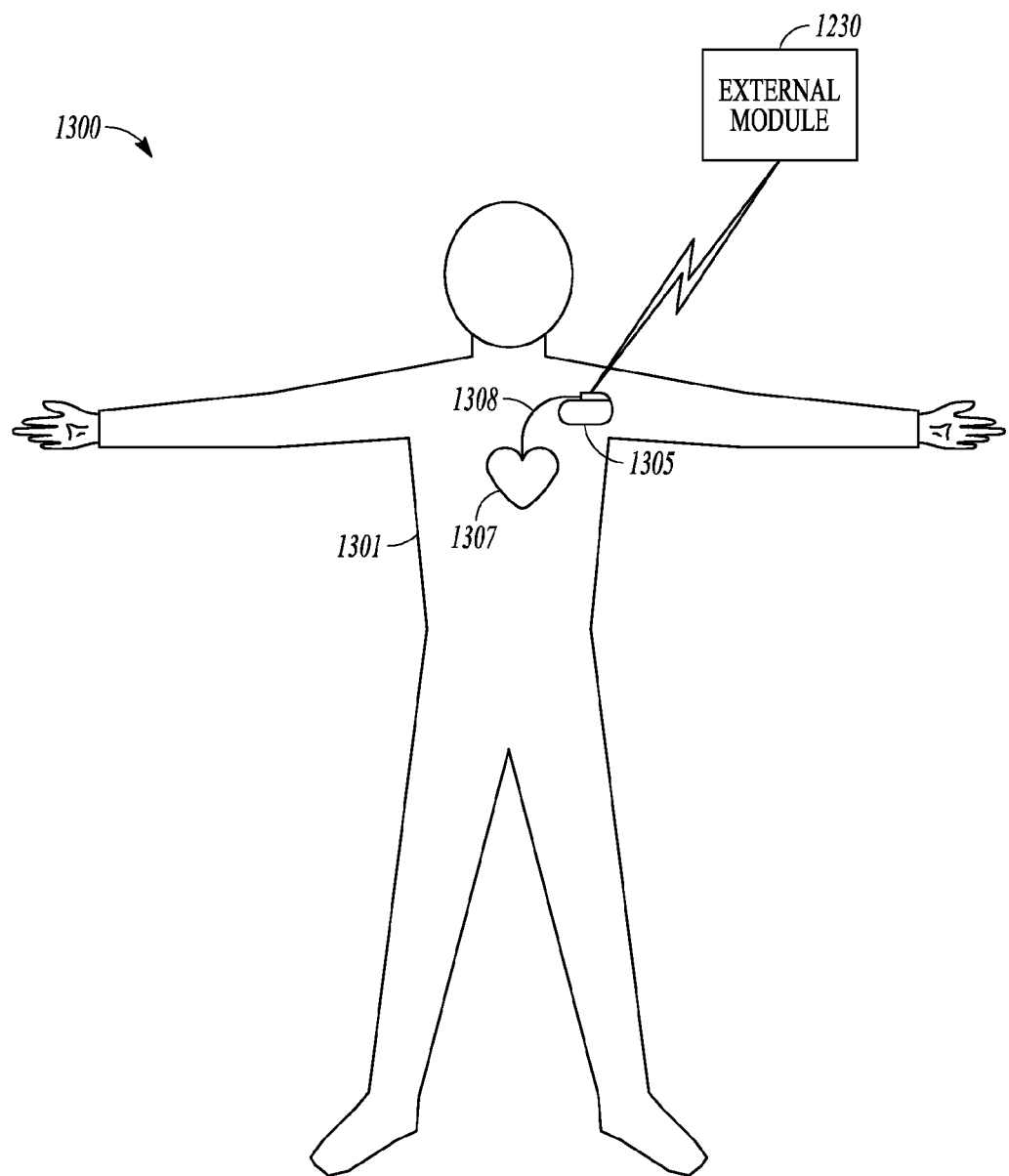
FIG. 13 illustrates generally an example of an implantable medical device that can provide a heart sound expectation window function.

FIG. 13 illustrates generally an example of a medical device system 1300 that can be communicatively coupled with the external module 1230. FIG. 13 further illustrates a patient 1301 with a heart 1307. In an example, the system 1300 can include an implantable medical device 1305 or a lead system 1308. Data or other instructions may be transferred between the device 1305 and the external module 1230 via a wireless telemetry link. Information transferred between the device 1305 and the external module 1230 may include data input to or data output from a patient or clinician, such as via the telemetry circuit 1224.

In an example, all or a portion of the functionality of the device 1200 can be provided in the device 1305. For example, one or more of the physiologic sensors 1250 can be included in the device 1305. In an example, one or more of the physiologic sensors 1250 can be coupled to the device 1305 but disposed in or on the patient 1301. For example, the blood pressure detector 1256 can be disposed in an artery of the patient 1301 and communicatively coupled to the device 1305.

VARIOUS NOTES & EXAMPLES

Example 1 can include subject matter (such as an apparatus, a method, a means for performing acts, or a device readable medium including instructions that, when performed by the device, can cause the device to perform acts), such as can include or use an apparatus, such as a medical device. The apparatus can include a heart sound processor circuit. The heart sound processor circuit can be configured to receive a heart sound signal of a patient. In an example, the heart sound processor circuit can be configured to obtain an initial heart sound expectation window function that describes a heart sound timing, of a specified type of heart sound, as a function of at least one physiologic variable. The physiologic variable can include at least one of a heart rate, information about an intrinsic vs. non-intrinsic beat, a respiration rate, an index of circadian timing, or posture. The function can include at least one characteristic parameter that can describe a value of a heart sound timing at a specified value of the at least one physiologic variable. In an example, the heart sound processor circuit can be configured to detect a patient heart sound, of the specified type, using the initial heart sound expectation window function and the heart sound signal. The heart sound processor circuit can be configured to update the at least one characteristic parameter using timing information from the detected patient heart sound of the specified type. The heart sound processor circuit can be configured to provide an updated heart sound expectation window function, using the updated at least one characteristic parameter, for subsequent use in detecting a patient heart sound of the specified type.

Example 2 can include, or can optionally be combined with the subject matter of Example 1 to optionally include an initial heart sound expectation window function that can describe an expected S2 heart sound timing. The initial function can be a linear function of heart rate. The at least one characteristic parameter can describe a value of an S2 heart sound timing at a specified heart rate. The at least one characteristic parameter can include at least one of a characteristic intercept parameter of the linear function or a characteristic slope parameter of the linear function. The heart sound processor circuit can be configured to detect an S2 patient heart sound and use timing information from the detected S2 patient heart sound to update at least one of the characteristic intercept parameter or the characteristic slope parameter. The heart sound processor circuit can be configured to provide an updated S2 heart sound expectation window function, using the updated at least one characteristic parameter, for subsequent use in detecting the patient's S2 heart sound.

Example 3 can include, or can optionally be combined with the subject matter of one or any combination of Examples 1 or 2 to optionally include, the heart sound processor circuit configured to obtain, as the initial heart sound expectation window function that describes the heart sound timing, an intrinsic S2 heart sound expectation window function that describes an S2 heart sound timing for an intrinsic beat. The function that describes the S2 heart sound timing for an intrinsic beat can be a linear function of heart rate. The heart sound processor circuit can be configured to obtain a non-intrinsic S2 heart sound expectation window function that describes an S2 heart sound timing for a non-intrinsic beat. The function that describes the S2 heart sound timing for a non-intrinsic beat can be a linear function of heart rate. The intrinsic and non-intrinsic heart sound expectation window functions can include respective first and second characteristic parameters. The heart sound processor circuit can be configured to detect an S2 patient heart sound using at least one of the intrinsic or non-intrinsic S2 heart sound expectation window functions, such as selected according to whether a beat is intrinsic or non-intrinsic. The heart sound processor circuit can be configured to update at least one of the first or second characteristic parameters using timing information from a detected S2 patient heart sound. The heart sound processor circuit can be configured to provide an updated S2 heart sound expectation window function using the updated at least one of the first or second characteristic parameters.

Example 4 can include, or can optionally be combined with the subject matter of one or any combination of Examples 1 through 3 to optionally include, an initial heart sound expectation window function describes an S2 heart sound timing as a function of at least one physiologic variable.

Example 5 can include, or can optionally be combined with the subject matter of one or any combination of Examples 1 through 4 to optionally include, a heart sound processor circuit that can be configured to obtain, as an initial heart sound expectation window function that describes a heart sound timing, an intrinsic S1 heart sound expectation window function that describes an S1 heart sound timing for an intrinsic beat, or a non-intrinsic S1 heart sound expectation window function that describes an S1 heart sound timing for a non-intrinsic beat. The intrinsic and non-intrinsic heart sound expectation window functions can include respective first and second characteristic parameters. The heart sound processor circuit can be configured to detect an S1 patient heart sound using at least one of the intrinsic or non-intrinsic S1 heart sound expectation window functions, such as can be selected according to whether a beat is intrinsic or non-intrinsic. The heart sound processor circuit can be configured to update at least one of the first or second characteristic parameters using timing information from the detected S1 patient heart sound. The heart sound processor circuit can be configured to provide an updated S1 heart sound expectation window function using an updated characteristic parameter, such as using at least one of the first or second characteristic parameters.

Example 6 can include, or can optionally be combined with the subject matter of one or any combination of Examples 1 through 5 to optionally include, a heart sound processor that can be configured to obtain, as an initial heart sound expectation window function, a function corresponding to a specified patient population of which a specified patient is a member.

Example 7 can include, or can optionally be combined with the subject matter of one or any combination of Examples 1 through 6 to optionally include a heart sound processor circuit that can be configured to obtain, as a function corresponding to a specified patient population, a function that is individualized to a patient.

Example 8 can include, or can optionally be combined with the subject matter of one or any combination of Examples 1 through 7 to optionally include, a heart sound processor circuit that can be configured to provide an updated heart sound expectation window function that can have an updated central value of the function at a specified value of a physiologic variable.

Example 9 can include, or can optionally be combined with the subject matter of one or any combination of Examples 1 through 8 to optionally include, a heart sound processor circuit that can be configured to provide an updated heart sound expectation window function for subsequent use in detecting a patient heart sound of a specified type, and for subsequent use in detecting at least one additional patient heart sound that is not of the same specified type.

Example 10 can include, or can optionally be combined with the subject matter of one or any combination of Examples 1 through 9 to optionally include, a heart sound processor circuit that can be configured to obtain, as an initial heart sound expectation window function, an S2 heart sound expectation window function. The heart sound processor circuit can be configured to provide, as the updated heart sound expectation window function, an updated S2 heart sound expectation window function for subsequent use in detecting an S2 heart sound. The heart sound processor circuit can be configured to provide an S3 heart sound expectation window function, such as using the updated S2 heart sound expectation window function, for subsequent use in detecting an S3 patient heart sound.

Example 11 can include, or can optionally be combined with the subject matter of one or any combination of Examples 1 through 10 to optionally include, a heart sound processor circuit that can be configured to obtain, as an initial heart sound expectation window function, an S2 heart sound expectation window function. The heart sound processor circuit can be configured to provide an updated S2 heart sound expectation window function for subsequent use in detecting an S2 heart sound. The heart sound processor circuit can be configured to provide an S4 heart sound expectation window function, using the updated S2 heart sound expectation window function, for subsequent use in detecting an S4 patient heart sound.

Example 12 can include, or can optionally be combined with the subject matter of one or any combination of Examples 1 through 11 to optionally include, a sensor configured to sense cardiac acoustic energy fluctuations or provide a heart sound signal.

Example 13 can include, or can optionally be combined with the subject matter of one or any combination of Examples 1 through 12 to optionally include, an auxiliary patient sensor that can be configured to provide at least one of patient posture information, patient physical activity level information, or patient respiratory status information. A heart sound processor circuit can be configured to provide an updated heart sound expectation window function using an updated characteristic parameter or at least one of the patient posture information, the patient physical activity level information, or the patient respiratory status information.

Example 14 can include, or can optionally be combined with the subject matter of one or any combination of Examples 1 through 13 to optionally include a physiologic variable that can include a patient heart rate.

Example 15 can include, or can optionally be combined with the subject matter of one or any combination of Examples 1 through 14 to optionally include a physiologic variable that can include information indicating intrinsic vs. non-intrinsic beat.

Example 16 can include, or can optionally be combined with the subject matter of one or any combination of Examples 1 through 15 to optionally include a physiologic variable that can include an index of circadian timing.

Example 17 can include, or can optionally be combined with the subject matter of one or any combination of Examples 1 through 16 to optionally include a physiologic variable that can include a patient posture status.

Example 18 can include, or can optionally be combined with the subject matter of one or any combination of Examples 1 through 17 to optionally include a heart sound processor circuit that can be configured to receive a heart sound signal. The heart sound processor circuit can be configured to obtain an initial S2 heart sound expectation window function that describes a patient S2 heart sound timing as a function of a physiologic variable selected from the group consisting of heart rate, intrinsic vs. non-intrinsic beat, respiration rate, index of circadian timing, and posture. The function can include a characteristic parameter, such as can be used to describe a value of the patient S2 heart sound timing at a specified value of the physiologic variable. The heart sound processor circuit can be configured to detect an S2 patient heart sound using the initial S2 heart sound expectation window function and the heart sound signal. The heart sound processor circuit can be configured to update the characteristic parameter using timing information from the detected S2 patient heart sound. The heart sound processor circuit can be configured to provide an updated S2 heart sound expectation window function, using the updated characteristic parameter, for subsequent use in detecting a patient S2 heart sound. The heart sound processor circuit can be configured to provide at least one of an S3 heart sound expectation window function or an S4 heart sound expectation window function, using the updated S2 heart sound expectation window function, such as for subsequent use in detecting a patient S3 or S4 heart sound.

Example 19 can include, or can optionally be combined with the subject matter of one or any combination of Examples 1 through 18 to optionally include subject matter (such as an apparatus, a method, a means for performing acts, or a device readable medium including instructions that, when performed by the device, can cause the device to perform acts), such as can include obtaining an initial heart sound expectation window function that describes a heart sound timing, of a specified type of heart sound, as a function of at least one physiologic variable. The physiologic variable can comprise at least one of a heart rate, intrinsic vs. non-intrinsic beat, respiration rate, index of circadian timing, or posture. The function can comprise at least one characteristic parameter that can describe a value of the heart sound timing at a specified value of the physiologic variable. Example 19 can optionally include detecting a patient heart sound, of the specified type, using the initial heart sound expectation window function, Example 19 can optionally include updating the at least one characteristic parameter using timing information from the detected patient heart sound of the specified type. Example 19 can optionally include providing an updated heart sound expectation window function, using the updated at least one characteristic parameter, for subsequent use in detecting a patient heart sound of the specified type.

Example 20 can include, or can optionally be combined with the subject matter of one or any combination of Examples 1 through 19 to optionally include obtaining an S2 heart sound expectation window function that can describe an S2 heart sound timing. The S2 heart sound expectation window function can be a linear function of heart rate. The linear function can include at least one of a characteristic intercept parameter or a characteristic slope parameter. The characteristic parameter(s) can describe a value of the S2 heart sound timing at a specified heart rate. Example 20 can include detecting an S2 patient heart sound using the S2 heart sound expectation window function. Example 20 can include using timing information from the detected S2 patient heart sound to update at least one of the characteristic intercept parameter or the characteristic slope parameter. Example 20 can include providing an updated S2 heart sound expectation window function, using the updated at least one characteristic parameter, for subsequent use in detecting an S2 patient heart sound.

Example 21 can include, or can optionally be combined with the subject matter of one or any combination of Examples 1 through 20 to optionally include providing at least one of an S3 heart sound expectation window function or an S4 heart sound expectation window function, such as using an updated heart sound expectation window function, such as for subsequent use in detecting a patient S3 or S4 heart sound.

Example 22 can include, or can optionally be combined with the subject matter of one or any combination of Examples 1 through 21 to optionally include obtaining an intrinsic S1 heart sound expectation window function that describes an S1 heart sound timing for an intrinsic beat, or obtaining a non-intrinsic S1 heart sound expectation window function that describes an S1 heart sound timing for a non-intrinsic beat. The intrinsic or non-intrinsic S1 heart sound expectation window functions can include respective first and second characteristic parameters. Example 22 can include detecting an S1 patient heart sound using at least one of the intrinsic or non-intrinsic S1 heart sound expectation window functions, selected according to whether a beat is intrinsic or non-intrinsic. Example 22 can include updating at least one of the first or second characteristic parameters using timing information from the detected S1 patient heart sound. Example 22 can include providing, using the updated at least one characteristic parameter, at least one of an updated intrinsic S1 heart sound expectation window function, or an updated non-intrinsic S1 heart sound expectation window function.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first" and "second" are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
   a sensor configured to sense a heart sound signal of a patient; and
   a heart sound processor circuit, configured to:
   receive the heart sound signal;
   obtain an initial heart sound expectation window function that describes a heart sound timing, of a specified type of heart sound, as a first function of at least one physiologic variable, the physiologic variable comprising at least one of intrinsic vs. non-intrinsic beat, respiration rate, index of circadian timing, or posture, and the first function comprising at least one characteristic parameter that describes a value of the heart sound timing of the specified type of heart sound at a specified value of the physiologic variable;
   detect a patient heart sound, of the specified type, using the initial heart sound expectation window function and the heart sound signal;
   update the at least one characteristic parameter using timing information from the detected patient heart sound of the specified type; and
   provide an updated heart sound expectation window function, using the updated at least one characteristic parameter, for subsequent use in detecting a patient heart sound of the specified type, the updated heart sound expectation window function describing the heart sound timing, of the specified type of heart sound, as a second function different from the first function of the at least one physiologic variable.

2. The apparatus of claim 1, wherein the initial heart sound expectation window function describes an expected S2 heart sound timing as a first function of the at least one physiologic variable and a heart rate, the first function including a linear function of heart rate, the at least one characteristic parameter describes a value of an S2 heart sound timing at a specified heart rate, and the at least one characteristic parameter includes at least one of a characteristic intercept parameter of the linear function or a characteristic slope parameter of the linear function; and
   wherein the heart sound processor circuit is configured to:
   detect an S2 patient heart sound;
   use timing information from the detected S2 patient heart sound to update at least one of the characteristic intercept parameter or the characteristic slope parameter; and
   provide an updated S2 heart sound expectation window function, using the updated at least one characteristic parameter, for subsequent use in detecting the patient's S2 heart sound.

3. The apparatus of claim 1, wherein the heart sound processor circuit is configured to:
   obtain, as the initial heart sound expectation window function that describes the heart sound timing, an intrinsic S2 heart sound expectation window function that describes an S2 heart sound timing for an intrinsic beat and is a linear function of heart rate, and a non-intrinsic S2 heart sound expectation window function that describes an S2 heart sound timing for a non-intrinsic beat and is a linear function of heart rate, the intrinsic and non-intrinsic heart sound expectation window functions including respective first and second characteristic parameters;
   detect an S2 patient heart sound using at least one of the intrinsic or non-intrinsic S2 heart sound expectation window functions, selected according to whether a beat is intrinsic or non-intrinsic;
   update at least one of the first or second characteristic parameters using timing information from the detected S2 patient heart sound; and
   provide an updated S2 heart sound expectation window function using the updated at least one of the first or second characteristic parameters.

4. The apparatus of claim 1, wherein the initial heart sound expectation window function describes an S2 heart sound timing as a function of the at least one physiologic variable.

5. The apparatus of claim 1, wherein the heart sound processor circuit is configured to:
   obtain, as the initial heart sound expectation window function that describes the heart sound timing, an intrinsic Si heart sound expectation window function that describes an S1 heart sound timing for an intrinsic beat, and a non-intrinsic S1 heart sound expectation window function that describes an S1 heart sound timing for a non-intrinsic beat, the intrinsic and non-intrinsic heart sound expectation window functions including respective first and second characteristic parameters;
   detect an S1 patient heart sound using at least one of the intrinsic or non-intrinsic S1 heart sound expectation window functions, selected according to whether a beat is intrinsic or non-intrinsic;
   update at least one of the first or second characteristic parameters using timing information from the detected S1 patient heart sound; and
   provide an updated S1 heart sound expectation window function using the updated at least one of the first or second characteristic parameters.

6. The apparatus of claim 1, wherein the heart sound processor circuit is configured to obtain, as the initial heart sound expectation window function, a function corresponding to a specified patient population of which the patient is a member.

7. The apparatus of claim 6, wherein the heart sound processor circuit is configured to obtain, as the function corresponding to the specified patient population, a function that is individualized to the patient.

8. The apparatus of claim 1, wherein the heart sound processor circuit is configured to provide the updated heart sound expectation window function to have an updated central value of the function at the same specified value of the physiologic variable.

9. The apparatus of claim 1, wherein the heart sound processor circuit is configured to provide the updated heart sound expectation window function for subsequent use in detecting a patient heart sound of the specified type, and for subsequent use in detecting at least one additional patient heart sound that is not of the same specified type.

10. The apparatus of claim 1, wherein the heart sound processor circuit is configured to obtain, as the initial heart sound expectation window function, an S2 heart sound expectation window function, and provide, as the updated heart sound expectation window function, an updated S2 heart sound expectation window function for subsequent use in detecting an S2 heart sound; and
   wherein the heart sound processor circuit is configured to provide an S3 heart sound expectation window function, using the updated S2 heart sound expectation window function, for subsequent use in detecting an S3 patient heart sound.

11. The apparatus of claim 1, wherein the heart sound processor circuit is configured to obtain, as the initial heart sound expectation window function, an S2 heart sound expectation window function, and provide, as the updated heart sound expectation window function, an updated S2 heart sound expectation window function for subsequent use in detecting an S2 heart sound; and wherein the heart sound processor circuit is configured to provide an S4 heart sound expectation window function, using the updated S2 heart sound expectation window function, for subsequent use in detecting an S4 patient heart sound.

12. The apparatus of claim 1, wherein the sensor is configured to sense cardiac acoustic energy fluctuations and provide the heart sound signal.

13. The apparatus of claim 12, further comprising an auxiliary patient sensor configured to provide at least one of patient posture information, patient physical activity level information, or patient respiratory status information, wherein the heart sound processor circuit is configured to provide the updated heart sound expectation window function using the updated at least one characteristic parameter and at least one of the patient posture information, the patient physical activity level information, or the patient respiratory status information.

14. The apparatus of claim 1, wherein the initial heart sound expectation window function describes the heart sound timing as a first function of the at least one physiologic variable and a patient heart rate.

15. The apparatus of claim 1, wherein the physiologic variable includes information indicating intrinsic vs. non-intrinsic beat.

16. The apparatus of claim 1, wherein the physiologic variable is an index of circadian timing.

17. The apparatus of claim 1, wherein the physiologic variable is a patient posture status.

18. An apparatus comprising:
a sensor configured to sense a heart sound signal of a patient; and
a heart sound processor circuit, configured to:
receive the heart sound signal;
obtain an initial S2 heart sound expectation window function that describes a patient S2 heart sound timing as a first function of a physiologic variable selected from the group consisting of intrinsic vs. non-intrinsic beat, respiration rate, index of circadian timing, and posture, the first function including a characteristic parameter, the characteristic parameter describing a value of the patient S2 heart sound timing at a specified value of the physiologic variable;
detect an S2 patient heart sound using the initial S2 heart sound expectation window function and the heart sound signal;
update the characteristic parameter using timing information from the detected S2 patient heart sound; and
provide an updated S2 heart sound expectation window function, using the updated characteristic parameter, for subsequent use in detecting a patient S2 heart sound, the updated S2 heart sound expectation window function describing the S2 heart sound timing as a second function different from the first function of the at least one physiologic variable; and provide at least one of an S3 heart sound expectation window function or an S4 heart sound expectation window function, using the updated S2 heart sound expectation window function, for subsequent use in detecting a patient S3 or S4 heart sound.

19. A method comprising:
obtaining an initial heart sound expectation window function that describes a heart sound timing, of a specified type of heart sound, as a first function of at least one physiologic variable, the physiologic variable comprising at least one of intrinsic vs. non-intrinsic beat, respiration rate, index of circadian timing, or posture, and the first function comprising at least one characteristic parameter that describes a value of the heart sound timing of the specified type of heart sound at a specified value of the physiologic variable;

detecting, using a sensor, a patient heart sound, of the specified type, using the initial heart sound expectation window function;

updating the at least one characteristic parameter using timing information from the detected patient heart sound of the specified type; and providing an updated heart sound expectation window function, using the updated at least one characteristic parameter, for subsequent use in detecting a patient heart sound of the specified type, the updated heart sound expectation window function describing the heart sound timing, of the specified type of heart sound, as a second function different from the first function of the selected physiologic variable.

20. The method of claim 19, wherein the obtaining the initial heart sound expectation window function that describes a heart sound timing includes obtaining an S2 heart sound expectation window function that describes an S2 heart sound timing as a first function of the at least one physiologic variable and a heart rate, the first function including a linear function of heart rate, the linear function including at least one of a characteristic intercept parameter or a characteristic slope parameter, the characteristic parameters describing a value of the S2 heart sound timing at a specified heart rate;

wherein the detecting the patient heart sound includes detecting an S2 patient heart sound using the S2 heart sound expectation window function;

wherein the updating the at least one characteristic parameter includes using timing information from the detected S2 patient heart sound to update at least one of the characteristic intercept parameter or the characteristic slope parameter; and wherein the providing the updated heart sound expectation window function includes providing an updated S2 heart sound expectation window function, using the updated at least one characteristic parameter, for subsequent use in detecting an S2 patient heart sound.

* * * * *